United States Patent
Duimstra et al.

(10) Patent No.: US 9,347,907 B2
(45) Date of Patent: *May 24, 2016

(54) DEVICE FOR PROVIDING A MEANS FOR INTERNAL CALIBRATION IN AN ELECTROCHEMICAL SENSOR

(71) Applicants: Joseph A. Duimstra, Belmont, CA (US); Lee Leonard, Mill Valley, CA (US); Gregory G. Wildgoose, Oxford (GB); Eric Lee, Sunnyvale, CA (US)

(72) Inventors: Joseph A. Duimstra, Belmont, CA (US); Lee Leonard, Mill Valley, CA (US); Gregory G. Wildgoose, Oxford (GB); Eric Lee, Sunnyvale, CA (US)

(73) Assignee: Senova Systems, Inc., Sunnyvale, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/503,140

(22) Filed: Sep. 30, 2014

(65) Prior Publication Data

US 2015/0198553 A1    Jul. 16, 2015

Related U.S. Application Data

(63) Continuation of application No. 13/255,224, filed as application No. PCT/US2010/026842 on Mar. 10, 2010, now Pat. No. 8,877,037.

(60) Provisional application No. 61/158,849, filed on Mar.

(Continued)

(51) Int. Cl.
*G01N 27/333* (2006.01)
*G01N 27/30* (2006.01)
(Continued)

(52) U.S. Cl.
CPC ............. *G01N 27/302* (2013.01); *B82Y 30/00* (2013.01); *C25B 11/00* (2013.01); *G01N 27/301* (2013.01); *G01N 27/333* (2013.01); *G01N 27/36* (2013.01); *Y10S 977/742* (2013.01)

(58) Field of Classification Search
CPC ... G01N 27/302; G01N 27/333; G01N 27/36; G01N 27/301; B82Y 30/00; C25B 11/00
See application file for complete search history.

(56) References Cited

U.S. PATENT DOCUMENTS 6,554,982 B1 * 4/2003 Shin ..................... G01N 27/301
                                                    204/401
7,135,342 B2   11/2006 Colvin, Jr. et al.
(Continued)

FOREIGN PATENT DOCUMENTS

JP    S55-135735    10/1980
JP    H01-136060     5/1989
(Continued)

OTHER PUBLICATIONS

Pauliukaite et al. (Electroanalysis 20, 2008, No. 5, 485-490).
(Continued)

*Primary Examiner* — Jennifer Dieterle
(74) *Attorney, Agent, or Firm* — David R. Conklin; Kirton McConkie

(57) ABSTRACT

Internally calibrated pH and other analyte sensors based on redox agents provide more accurate results when the redox active reference agent is in a constant chemical environment, yet separated from the solution being analyzed in such a way as to maintain electrical contact with the sample. Room temperature ionic liquids (RTIL) can be used to achieve these results when used as a salt bridge between the reference material and the sample being analyzed. The RTIL provides the constant chemical environment and ionic strength for the redox active material (RAM) and provides an electrolytic layer that limits or eliminates direct chemical interaction with the sample. A broad range of RAMs can be employed in a variety of configurations in such "Analyte Insensitive Electrode" devices.

15 Claims, 12 Drawing Sheets

Related U.S. Application Data 10, 2009, provisional application No. 61/163,139, filed on Mar. 25, 2009, provisional application No. 61/225,855, filed on Jul. 15, 2009, provisional application No. 61/289,318, filed on Dec. 22, 2009, provisional application No. 61/308,244, filed on Feb. 25, 2010, provisional application No. 61/309,182, filed on Mar. 1, 2010.

(51) Int. Cl.
 *B82Y 30/00* (2011.01)
 *C25B 11/00* (2006.01)
 *G01N 27/36* (2006.01)

(56) References Cited

U.S. PATENT DOCUMENTS

| | | | |
|---|---|---|---|
| 7,695,850 B2 | 4/2010 | Sotomura et al. | |
| 8,877,037 B2 * | 11/2014 | Duimstra | G01N 27/36 204/416 |
| 2005/0129939 A1 | 6/2005 | Shigematsu et al. | |
| 2005/0222277 A1 | 10/2005 | Kimizuka et al. | |
| 2006/0003457 A1 | 1/2006 | Porter et al. | |
| 2007/0082227 A1 | 4/2007 | Kobayashi et al. | |
| 2007/0272552 A1 | 11/2007 | Jiang et al. | |
| 2008/0035481 A1 | 2/2008 | McCormack et al. | |
| 2008/0302660 A1 | 12/2008 | Kahn et al. | |
| 2009/0178921 A1 | 7/2009 | Lawrence et al. | |
| 2009/0218239 A1 | 9/2009 | Gooding et al. | |
| 2009/0283404 A1 | 11/2009 | Kakiuchi et al. | |
| 2009/0294284 A1 * | 12/2009 | Hsiung | G01N 27/301 204/290.05 |

FOREIGN PATENT DOCUMENTS

| | | |
|---|---|---|
| JP | 2004-045279 | 2/2004 |
| WO | 2008/032790 A1 | 3/2008 |
| WO | 2008154409 A1 | 12/2008 |

OTHER PUBLICATIONS

Torabi et al. (Electroanalysis 19, 2007, No. 14, 1483-1489).

Cui et al. (Nanomedicine: Nanotechnology, Biology, and Medicine 1 (2005) 130-135).

Wildgoose, Gregory G. et al., "Abrasively Immobilised Multiwalled Carbon Nanotube Agglomerates: A Novel Electrode Material Approach for the Analytical Sensing of pH," ChemPhysChem, pp. 669-677, 2004.

Pizzariello, Andrea et al., "Urea Biosensor Based on Amperometric pH-Sensing with Hematein as a pH-Sensitive Redox Mediator," Talanta, Elsevier Science B.V., pp. 763-772, 2001.

Opdycke, W. N. et al., "Polymer-Membrane pH Electrodes as Internal Elements for Potentiometric Gas-Sensing Systems," Analytica Chinica Acta, 155, Elsevier Science Publishers B.V., pp. 11-20, 1983.

\* cited by examiner

AIMs TESTED

| Configuration | $^n$BuFc | AG-np-CG | Fc | PVFc | Ni HCF | Fc Styrene Copolymer | Fc Sty xlink Polymer | Ni Cyclam | $K_4Fe(CN)_6$ |
|---|---|---|---|---|---|---|---|---|---|
| 1 | X | X | X | X | X | X | X | X | X |
| 2 | X | NA | X | X | NA | X | X | X | NA |
| 3 | NA | NA | NA | NA | NA | NA | X | X | X |
| 4 | NA | X | NA | NA | X | X | X | NA | NA |

FIG. 3

DEVICE FOR PROVIDING A MEANS FOR INTERNAL CALIBRATION IN AN ELECTROCHEMICAL SENSOR

RELATED APPLICATIONS

This application is a continuation of U.S. patent application Ser. No. 13/255,224, filed Nov. 17, 2011 and titled DEVICE FOR PROVIDING A MEANS FOR INTERNAL CALIBRATION IN AN ELECTROCHEMICAL SENSOR, which application is a United States National Stage application of International Application No. PCT/US2010/026842, filed Mar. 10, 2010 and claiming priority from U.S. Provisional Application No. 61/158,849, filed Mar. 10, 2009, all of which are incorporated herein by reference.

BACKGROUND

The present invention provides methods and devices for measuring the concentration of an analyte in solution and relates to the field of chemistry.

Most conventional pH sensors on the market today utilize an ion sensitive glass bulb sensitive to pH and an internal reference electrode. The reference electrode is usually a chloridized silver (Ag|AgCl) wire immersed in potassium chloride (KCl) gel or liquid and separated from the sample being analyzed via a porous frit, as shown in the schematic in FIG. 1. Both the use of an internal reference electrode and the necessity for the inclusion of a porous frit impair the operation of these conventional glass pH probes due to problems with drift caused by changes in the reference electrode potential and fouling or blocking of the frit. Thus, these conventional pH probes require constant recalibration, the electrodes must be stored in a KCl solution to keep the porous frit from drying out, and the fragile glass membrane renders these probes unsuitable for many applications where pH measurement is required under conditions of high temperature or pressure.

Effort has been made to improve the function of the reference electrode by, for instance, modification of the electrode-analyte interface (see U.S. Pat. No. 7,276,142) or replacement of the typically heterogeneous redox couple (e.g. calomel or silver/silver chloride) with a homogeneous redox couple (e.g. iodide/triiodide) (see U.S. Pat. No. 4,495,050). These changes are based on the extension of the potentiometric reference electrode concept wherein the conventional reference electrode (CRE) typically comprises two halves of a redox couple in contact with an electrolyte of fixed ionic composition and ionic strength. Because both halves of the redox couple are present and the composition of all the species involved is fixed, the system is maintained at equilibrium and the potential drop (i.e. the measured voltage) across the electrode-electrolyte interface of the conventional reference electrode is then thermodynamically fixed and constant. The function of the reference electrode is then to provide a fixed potential to which other measurements, such as pH, may be compared.

While these conventional reference electrodes provide a stable potential, they suffer from many disadvantages. One disadvantage is the need for an electrolyte of fixed and known ionic composition and ionic strength, because any change in ionic composition or strength will result in a shift in equilibrium of the redox couple, thereby compromising the stability of the constant potential of the electrode. To preclude a change in electrolyte composition, the redox system and electrolyte are typically isolated from the sample under study via a porous frit or small aperture. This isolation introduces an additional disadvantage to the conventional reference electrode, namely the propensity for the frit or aperture to clog, rendering the electrode useless. These disadvantages are exacerbated by the fact that the electrolyte is typically an aqueous solution of high salt concentration, resulting in the requirement that the electrode frit or aperture must be kept wet to avoid clogging due to salt precipitation.

A remarkable advance in pH sensor technology is the solid state internally calibrated pH sensor comprised of two redox-active pH sensitive agents (anthraquinone (AQ) and 9,10-phenanthrenequinone (PAQ)) and one pH insensitive redox agent (e.g., Ferrocene (Fc)); see PCT Patent Publication Nos. 2005/066618 and 2007/034131 and GB Patent Publication No. 2409902. In such sensors, all three redox agents may be mixed together with multiwalled carbon nanotubes (MWCNT), graphite powder and epoxy, and the resulting admixture cured and formed into solid sensors. When a voltage sweep is applied to the sensor and the resultant current measured (using square wave voltammetry, for example), one observes three peaks: one peak for each of the three redox agents.

In these solid state internally calibrated pH sensors, the pH insensitive peak (due to Fc) should ideally be constant and independent of pH or ionic species in solution and should not drift over time. The AQ and PAQ peaks should ideally vary their position on the voltage sweep in a predictable fashion depending on the pH of the solution being measured. Finally, the positions of the pH sensitive peaks, when compared to the position of the pH insensitive peak, allow the solution pH to be deduced by comparing those values to a calibration table. For this system to have the greatest accuracy and so have the greatest scope of application, the pH insensitive peak must be stable over time, and its peak position must be unaffected by varying solution compositions. Otherwise, the accuracy of the system is compromised. Unfortunately, most if not all pH insensitive redox agents appear to be affected unsuitably by different ions and exhibit significant drift or shifts in peak position. This problem is also present in other sensors that respond to analytes other than pH. Accordingly, there remains a need in the art for materials and methods for making internally calibrated pH and other analyte sensors based on redox agents.

The present invention meets this need.

SUMMARY OF THE INVENTION

The present invention arises in part from the discoveries that (i) the pH insensitive material, or more generally, the analyte insensitive material (AIM), must be maintained in a constant chemical environment, yet separated from the solution being analyzed in such a way as to maintain electrical contact with the sample being analyzed; (ii) an electrolytic layer, which can be composed of, for example and without limitation, room temperature ionic liquids (RTIL) or other ionic liquids or liquids with sufficient ionic strength, can be used to achieve the desired results when used as a salt bridge between the AIM and the sample being analyzed; and (iii) with such an electrolytic layer, an analyte sensitive material (ASM) can be used in place of or in addition to an AIM, because the ASM is converted functionally into an AIM when a suitable electrolytic layer is employed. The electrolytic layer (e.g. composed of an RTIL or other suitable material, as described herein) provides the constant chemical environment and ionic strength for the AIM (or ASM) and provides a layer that limits or eliminates direct chemical interaction with the sample being analyzed. A broad range of redox active materials can be employed in a variety of configurations in accordance with the methods and in the "analyte insensitive electrodes" (AIEs) of this invention and devices containing them.

The present invention provides a variety of AIEs for use in the internally calibrated pH and other analyte sensors based on redox agents provided by the invention. The schematic shown in FIG. 2 provides illustrative embodiments of this aspect of the invention. In that figure, the oval dots represent the redox active material. Additional embodiments are also provided and will be apparent to one of skill in the art upon consideration of this disclosure; for example, in some embodiments, the electrolytic layer (e.g. RTIL or other material) is in a porous structure or "conductive physical barrier", which serves to limit direct chemical interaction and enhance electronic communication between the sample test solution and the redox active material.

A wide variety of redox active materials (e.g. AIMs or ASMs) can be used and placed in the different configurations of the various embodiments of the sensors of the invention, depending on the application for which a device is intended and the solubility and/or other characteristics of the redox active material. For example, redox active materials that have been tested and demonstrated to be useful in the methods and devices of the invention are shown in FIG. 3.

Thus, the invention relates to compositions, devices, electrodes, sensors, systems, and methods useful for detecting the presence of an analyte or measuring the analyte concentration in a sample. In one aspect, the invention provides a means of continuous internal self-calibration for such measurements. In one aspect, the invention provides a substantially analyte insensitive electrode (AIE), and in one embodiment, this electrode employs a substantially analyte insensitive redox active material (AIM) to generate a predictable analyte insensitive signal, while in another embodiment, this electrode employs a substantially analyte sensitive redox active material (ASM) to generate a predictable analyte insensitive signal. In another aspect, the invention provides a voltammetric or amperometric analyte sensor system in which an AIE of the invention generates a signal that is compared with an analyte sensitive signal from an analyte sensitive electrode (ASE) to provide a means for continuous internal self-calibration.

The present invention thus meets the need for an AIE capable of generating a substantially analyte insensitive signal in response to the application of an electrical stimulus applied to the sample being analyzed in the course of making voltammetric or amperometric measurements of analyte concentration in the sample. The electrodes of the invention provide a predictable signal useful as an internal standard (in other words, a standard internal to the system) with which an analyte sensitive signal may be continuously compared, and therefore permit greater accuracy and reproducibility in determining analyte concentration.

The present invention therefore provides an AIE that can be used in an electrochemical analyte sensing device that is capable of generating a substantially analyte-insensitive electrical response when an electrical stimulus is applied to an analyte sample in the course of making voltammetric and/or amperometric measurements of analyte concentration.

The invention also provides a self-calibrating electrochemical analyte sensor system which incorporates such an electrode. The invention also provides a method of using such an electrode as an internal self-calibrating standard in an analyte sensor system, e.g. for the purpose of making voltammetric and/or amperometric measurements to determine the presence and/or concentration of an analyte in a sample. The invention also provides a method of making such an AIE.

The invention also provides a multi-phase AIE for use in an electrochemical sensing device for measuring an analyte in a sample, comprising: (a) a first phase comprising an electrolytic layer (which can be, for example and without limitation, an ionic liquid (IL), which in one embodiment is a liquid comprised solely of ions, wherein the IL phase is adjacent to the sample and substantially immiscible with the sample), (b) an electrically conductive component electrically connected to the electrolytic layer, and (c) a redox active material (RAM), capable of being electrochemically oxidized and/or electrochemically reduced, wherein the redox activity of the redox active material is substantially insensitive to the analyte, and wherein further the redox active material may be dispersed in either the electrolytic layer or the conductive component.

In some embodiments of the invention, the electrolytic layer is an IL, such as a room temperature IL (RTIL), i.e. a liquid comprised entirely of ions which is liquid at temperatures below 100 degrees Celsius. In some embodiments, the RTIL is N-butyl-N-methyl pyrrolidinium bis(trifluoromethanesulfonyl)imide (C4mpyrrNTf2).

In various embodiments of the invention, the analyte is dispersed in a liquid sample, and/or is an ion dispersed in a liquid sample, and/or is hydrogen ion. In some embodiments, the analyte is a non-ionic species dispersed in a liquid species. In one aspect of the invention, the redox active material in the AIE is selected from the group consisting of redox-active organic molecules, redox-active polymers, metal complexes, organometallic species, metals, metal salts, or semiconductors, and undergoes one or more electron transfer processes not involving any reaction or chemical interaction with the target analyte. In some embodiments, the redox active material in the AIE is n-butyl-ferrocene. In other embodiments, the redox active material in the AIE is $K_4Fe(CN)_6$.

In some embodiments of the invention, the conductive component comprises an electrically conductive material selected from the group consisting of carbon allotropes and derivatives thereof, transition metals and derivatives thereof, post-transition metals and derivatives thereof, conductive metal alloys and derivatives thereof, silicon and derivatives thereof, conductive polymeric compounds and derivatives thereof, and semiconductor materials and derivatives thereof. In other embodiments of the invention, the conductive component further comprises a composite material comprising a binder and an electrically conductive material. In some embodiments of the invention, the electrically conductive material present in the composite material comprises graphite and/or glassy carbon, and/or multi-walled carbon nanotubes (MWCNTs) and/or single-walled carbon nanotubes (SWCNTs), and/or any combination thereof. In other embodiments of the invention, the composite material further comprises a redox active material. In one aspect, the redox active material is n-butyl-ferrocene. In other embodiments of the invention, the composite material comprises a redox-active ASM with conferred analyte insensitivity as a consequence of the AIE construct.

In some embodiments of the invention, the AIE further comprises a conductive physical barrier adjacent to the sample, for physically separating the electrolytic layer (e.g. IL phase) from the sample. In some embodiments of the invention, the conductive physical barrier is selectively impermeable to the analyte. In some embodiments of the invention, the conductive physical barrier is selectively permeable or selectively impermeable to non-analyte species in the sample. In other embodiments of the invention, the conductive physical barrier is a porous frit. In some embodiments of the invention, the conductive physical barrier is a membrane. In other embodiments of the invention, the conductive physical barrier is a film.

In some embodiments of the invention, the AIE further comprises a second electrolytic layer adjacent to the first electrolytic layer interposed between the conductive component and the first electrolytic layer and in electrical connection with the conductive component and the first electrolytic layer, and a conductive physical barrier layer interposed between the first and second electrolytic layers, for physically separating the electrolytic layers from each other, wherein, optionally, the first electrolytic layer is substantially immiscible with the second electrolytic layer and wherein further the redox active material may also be dispersed in the second electrolytic layer. In other embodiments of the invention, the second electrolytic layer is selected from the group consisting of an aqueous electrolyte solution, a gelled aqueous electrolyte solution, an electrolytic sol gel, and an organic electrolyte solution.

The present invention further provides an electrochemical sensing device for measuring an analyte in a sample, comprising (a) an AIE as described above in any of its various embodiments, and (b) a working electrode in electrical connection with the AIE, and comprising a redox-active analyte sensitive material (ASM), capable of being electrically oxidized and/or electrically reduced, and wherein the redox activity of the ASM is substantially sensitive to the analyte. Working electrodes suitable for use in the sensing devices of the invention include, for example and without limitation, those described in provisional U.S. patent application Ser. No. 61/161,139, filed 25 Mar. 9; Ser. No. 61/225,855, filed 15 Jul. 9; and Ser. No. 61/289,318, filed 22 Dec. 9, each of which is incorporated herein by reference.

In some embodiments, the AIE and the working electrode are in parallel electrical connection. In other embodiments, the AIE and the working electrode are configurationally joined and electrically connected by a common conducting component. In another embodiment, the AIE and the working electrode are electrically connected within a single-channel electronic controlling device. In some embodiments, the AIE and the working electrode are connected on separate data channels within a multi-channel electronic controlling device.

In some embodiments, the electrochemical sensing device of the present invention further comprises an electronic device for generating and/or measuring an analytical signal. In another embodiment, the electrochemical sensing device of the present invention further comprises a conventional reference electrode or a pseudo-reference electrode.

The present invention further provides a method of using the sensing device of the present invention for measuring an analyte in a sample, comprising the steps of applying an electrical signal to the AIE, and measuring the electrical response of the AIE, wherein the electrical response of the AIE is independent of analyte concentration in the sample. In some embodiments, the measured electrical response of the AIE remains substantially constant over time and repeated use. In some embodiments, the measured electrical response of the AIE varies in a substantially predictable manner over time and repeated use. In some embodiments, the measured electrical response of the AIE remains substantially constant relative to a reference potential, independent of the analyte, upon application of the electrical signal to the AIE. In another embodiment, the measured electrical response of the AIE varies in a substantially predictable manner relative to a reference potential, independent of the analyte, upon application of the electrical signal to the AIE. In some embodiments, the measured electrical response of the AIE remains substantially constant relative to a known electrical response. In another embodiment, the measured electrical response of the AIE varies in a substantially predictable manner relative to a known electrical response.

These and other aspects and embodiments of the invention are described in the accompanying drawings, which are briefly described below and in the detailed description of the invention that follows.

BRIEF DESCRIPTION OF THE DRAWINGS

FIG. 3 shows a table presenting various AIM compounds that have been tested with various AIE configurations shown in FIG. 2. In the Figure, n-BuFc is n-butyl ferrocene; AG-np-CG is a silver nanoparticle-coated glassy carbon; PVFc is polyvinyl ferrocene; and NiHCF is nickel hexacyanoferrate.

FIG. 5A shows a plot of peak current vs. scan number measured over the course of 7000 oxidative scans at pH 7 (1000 scans=430 minutes). FIG. 5B shows a plot of scan number vs. peak potential for the same experiment. FIG. 5C shows the results from voltammetric measurements taken from a control experiment overlaid with the first 2000 scans from FIG. 5B. The control experiment is identical to the experiment used to generate the data in FIGS. 5A and 5B except that the electrolytic layers and conductive physical barriers are absent from the construct.

FIG. 6A shows pH buffer/KCl concentration vs. peak height measured over the course of 20 oxidative scans in several standard pH buffers as well as 10 mM aqueous KCl solution and 100 mM aqueous KCl solution. FIG. 6B shows a plot of pH buffer/KCl concentration vs. peak potential for the same experiment. FIG. 6C shows the same data as FIG. 6B but rescaled on the y-axis to allow a direct comparison to be made with the data in FIG. 6D. FIG. 6D shows a plot of pH buffer/KCl concentration vs. peak potential for the corresponding control experiment without the AIE construct (i.e. no RTIL in the construct). The peak potential scale for both FIGS. 6C and 6D is the same.

DETAILED DESCRIPTION OF THE INVENTION

Figure 1:
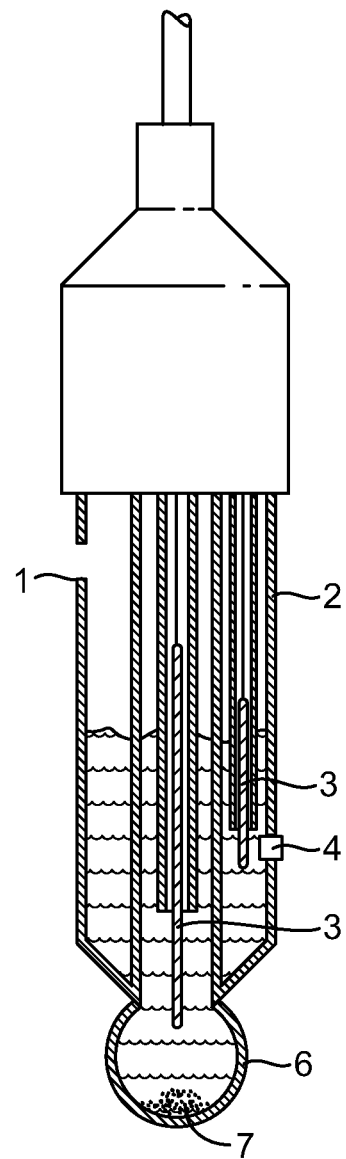
FIG. 1 shows a conventional glass pH electrode which incorporates a chloridized silver wire (Ag|AgCl) as the reference electrode.

In the following description of the invention, specific conditions recited, for example, to prepare materials incorporated into embodiments of the invention, may of course be varied in practice by those of skill in the art upon consideration of this disclosure. In general, the terminology used herein is for the purpose of describing particular embodiments only and is not intended to be limiting. As used herein, the singular forms "a," an" and "the" include plural referents unless the context clearly dictates otherwise. Thus, for example, reference to "a binder" includes mixtures of binders, and a reference to "a conductive material" may include more than one such material. The following paragraphs provide definitions for the convenience of the reader.

An "analyte" is a chemical species of interest present in a sample, the presence of which is detectable or the concentration of which is measurable by using an analyte sensor system which incorporates the AIE of the present invention as a self-calibrating internal standard that provides either a substantially constant or a predictable response during analyte sensing. "Substantially constant" is used to mean constant within a range defined by the end user.

A "redox active material" (RAM) is one that may be oxidized and/or reduced. "Redox activity" refers to either or both of those processes.

An "analyte insensitive material" (AIM), also known as a "chemically insensitive redox active material", is a redox active material that is insensitive, or substantially insensitive, to the presence or the concentration of an analyte in a sample. "Substantially insensitive" to an analyte is used to mean insensitive within the tolerances required for a given application, as those tolerances are defined by an end user. Conversely, an "analyte sensitive material" (ASM) is a redox active material that (when not in an AIE of the invention) is sensitive or substantially sensitive to the presence or concentration of an analyte in a sample within those user-defined application-specific tolerances. As discussed above, an ASM is functionally equivalent to an AIM when utilized in an AIE of the invention. Thus, any reference to an AIM (or ASM) should be considered to be a reference to an ASM (or AIM) in connection with a description of a redox active material for use in an AIE of the invention. Thus, when a redox active material is part of an AIE of the invention, the term RAM may be used to indicate that any redox active material (i.e. an AIE or an ASM) can be employed.

For a RAM to be "dispersed" means that it is dissolved in a solution or colloidally suspended in a gas, liquid or solid. The term is also intended to encompass embodiments wherein the RAM is abrasively immobilized, adsorbed, electrostatically bound or covalently bound to the surface of a solid or to a component of the solid. The term is also intended to encompass embodiments wherein the RAM is incorporated as a dopant in a crystal lattice. The term is also intended to encompass an intercalation of the RAM within a solid. In some embodiments of the invention, the RAM is dispersed in a membrane that serves as a conductive physical barrier.

An "electrochemical sensing system" is a system of electrodes which is capable of measuring the presence and/or concentration of an analyte in a sample. Such systems generally include a working electrode, a reference electrode (either a conventional or pseudo reference electrode) and a counter electrode. Optionally, e.g., in cases where the working electrode is a microelectrode, the system may include only a reference electrode and working electrode. Optionally, the system may include a controller/processor device.

A "working electrode" (WE) is the electrode at which the electrochemical process of interest occurs. In a sensor, the working electrode may be sensitive to one or more analyte(s) in the test solution, or it may be chemically modified with analyte sensitive species/materials. The electrochemical response of the working electrode is measured after some perturbation has been applied to the system under study. For example, the perturbation may be the application of a potential difference to the WE which induces electron transfer to occur, and the resulting current at the working electrode is then recorded as a function of either the applied potential (voltammetric mode) or time (chronoamperometric mode). These two examples of modes of operation are illustrative and not exhaustive; many other modes are known in the art.

An "analyte insensitive electrode" (AIE) is a special case of a working electrode where the current flow depends in part on redox processes that are independent of the presence or concentration of species (apart from a minimum threshold of supporting electrolyte) in the sample composition including but not limited to the analyte. AIEs of the invention are described in more detail below.

To monitor the potential difference applied to the WE, a reference point is required. This is provided by the use of a "reference electrode" (RE). Conventional reference electrodes (CREs) have a certain fixed chemical composition and therefore a fixed electrochemical potential, thus allowing measurement of the potential difference applied to the WE in a known, controlled manner. A CRE typically comprises two halves of a redox couple in contact with an electrolyte of fixed ionic composition and ionic strength. Because both halves of the redox couple are present and the composition of all the species involved is fixed, the system is maintained at equilibrium, and the potential drop (i.e. the measured voltage) across the electrode-electrolyte interface of the CRE is then thermodynamically fixed and constant. For example a commonly used CRE system is the Ag|AgCl|KCl system with a defined and constant concentration of KCl. The two half-cell reactions are therefore: $Ag^+ + e^- \rightarrow Ag$; and $AgCl + e^- \rightarrow Ag + Cl^-$. The overall cell reaction is therefore: $AgCl \rightarrow Ag^+ + Cl^-$ for which the Nernst equilibrium potential is given as: $E = E^0 - (RT/F)*\ln[Cl^-]$ where E is the measured RE potential, $E^0$ is the standard potential of the Ag|AgCl couple vs. the standard hydrogen electrode with all species at unit activity (by convention this is defined as having a potential of 0.0V), R, T and F are the universal gas constant, temperature and Faraday constant respectively in appropriate units. Hence the potential of this system depends only on the concentration (more strictly speaking the activity) of $Cl^-$ ion present, which, if this is fixed, provides a stable, fixed potential. Many other CRE systems are known in the art. It is imperative that the composition of the CRE remains constant, and hence almost no current should be passed through the CRE (otherwise electrolysis will occur and the composition of the CRE will change), which necessitates the use of a third electrode, the counter electrode (CE) to complete the circuit. However, two-electrode configurations can be used in the special case where the WE is a microelectrode, having at least one dimension typically smaller than 100 microns. In this case, the currents passed at the WE are small, and therefore a two-electrode cell can be used with a CRE, but without the need for a CE.

The term "pseudo-reference electrode" (PRE) refers to a type of reference electrode which is sometimes used, particularly in non-aqueous electrolytes. These electrodes typically do not comprise both halves of a well-defined redox potential and are therefore not thermodynamic reference electrodes of fixed composition and potential. However, they provide a reasonably constant potential over the timescale of an electrochemical experiment (on the order of minutes), and the absolute potential of the PRE can then be calibrated back to a CRE if required. One example of a PRE is a silver wire (used commonly in non-aqueous electrochemistry).

To pass current through the cell, one further electrode is required to complete the circuit, known as a "counter electrode" (CE) or sometimes an "auxiliary electrode". This electrode simply serves as a source or sink of electrons and allows current to flow through the cell. To avoid unwanted electrochemical redox processes occurring at the CE, which may interfere with the signal measured at the WE, CEs are typically made using relatively chemically inert materials, commonly Pt, but carbon (graphite) is also commonly employed.

A "conductive physical barrier" is a layer that is either adjacent to the sample being analyzed or is interposed between two adjacent phases of the AIE. A conductive physical barrier is "selectively impermeable" to a species in a sample when it prevents the species from passing through it but allows other components of the sample, such as charge carriers in the electrolyte component of the sample, to do so freely. Conversely, a conductive physical barrier is "selectively permeable" to a species in the sample when it allows the species to move freely across it. In some embodiments, the AIE may incorporate more than one conductive physical barrier as a means of physically separating the various components of the AIE from one another as well as from the sample being analyzed.

"Configurationally joined" denotes a direct physical connection between two or among several elements.

An "ionic liquid" (IL) is a liquid comprised principally of both cations and anions. In one embodiment, an "ionic liquid" (IL) is a liquid comprised entirely of both cations and anions. A "room temperature ionic liquid" (RTIL) is an IL that is a liquid at temperatures below 100 degrees Celsius.

Phases which are "adjacent" to another phase, i.e., to the conductive component or to the sample, may optionally be physically separated by an interface layer.

With these definitions in mind, one of ordinary skill in the art can better understand the organization and content of the following discussion of the invention. A description of the Analyte Insensitive Electrode (AIE) of the invention and its uses is followed by discussion of the individual components of the AIE, culminating in several exemplary embodiments of the AIE. Upon conclusion of the description of the AIE itself, an electrochemical sensing system that uses an AIE of the invention is then described, including a description of the various components of said system.

Prior to the present invention, typical voltammetric or amperometric electrochemical sensing systems typically comprised three electrodes, the working electrode, the reference electrode, and the counter electrode. Under conditions where little current flows through the sensing system, the reference and counter electrode functions can be combined into a single electrode resulting in a two-electrode system (working and reference/counter). Briefly, the sensing system functions by monitoring the current flow through the WE as a function of the applied potential. The applied potential is monitored by the RE, while the potential and current are supplied to the sample by the CE. The potential sensed by the RE is continuously compared with the desired waveform output by the controller/processor device. If the potential recorded by the RE does not reflect the desired potential, then the counter electrode is adjusted until the RE potential and the desired potential match. The accuracy of the current versus voltage response of the system therefore depends on the ability of the RE to measure the potential at the WE accurately. High accuracy thus necessitates a highly stable RE that effectively measures the potential without being affected by the sample or duration of measurement. The silver/silver chloride and saturated calomel electrodes are examples of such conventional reference electrodes (CREs).

As discussed above, CREs such as silver/silver chloride and saturated calomel electrodes have several disadvantages. There remains a need for a system that circumvents these disadvantages. The present invention addresses this by loosening the stability requirement of the RE via introduction of a fourth electrode, the AIE. Due to this relaxation in stability, simple pseudo reference electrodes (PREs), such as the silver wire, may be used as REs. Functionally the AIE behaves as an additional WE with the exception that the AIE response, being independent of analyte, is always fixed relative to a known response such as the standard hydrogen electrode (SHE). Thus, instability in a given RE can be corrected by comparison with the known fixed response of the AIE.

In comparison to examples from the prior art that include pH insensitive redox materials or other AIMs (see for instance WO2005/066618 or WO2005/085825), the utility of the AIE of the invention arises, at least in part, from its ability to improve the stability and longevity of the AIM across both time and analyte composition. These improvements act to increase the performance and scope of applicability of the AIM compared to the prior art. Furthermore, the AIE construct relaxes the requirement that the RAM employed be insensitive to pH or other analytes of interest, thus broadening the range of RAMs that may be used to include not only AIMs but ASMs as well.

Thus, in a first aspect, the present invention provides an electrode that renders redox materials contained therein insensitive to non-electrical external influences (e.g. analyte concentrations) while maintaining electrical contact with the balance of the components of the sensing system. The electrode of the invention is therefore an analyte insensitive electrode (AIE). Due to this analyte insensitivity, the signal response of the AIE is independent of the environment in which the sensing system is placed, and therefore can be used as an internal calibration point. The AIE can comprise a redox active material that is itself insensitive to the analyte (i.e. an analyte insensitive material or AIM) independent from the construct. Due to the nature of the construct, however, it is not a requirement that the redox material be insensitive to the analyte independent of the construct. In this case, for example, the AIE may comprise a redox material which is itself sensitive to the analyte (i.e. an analyte sensitive material or ASM) independent from the construct, but which is rendered insensitive to the analyte when used as the redox component of the AIE.

Analyte Insensitive Electrode (AIE)

An AIE of the present invention can be viewed as a special class of WE in that it operates in much the same way as the WE described above, except that the measured AIE response is substantially insensitive to changes in the composition and/or presence of analyte(s) within the test solution. It does, however, comprise a redox-active species and so provides an electrochemical response, but one which is independent of any changes to the test solution composition (apart from a minimum threshold of supporting electrolyte) or the presence of any analyte. Thus, the AIE provides a constant, fixed electrochemical response, the nature of which depends on the mode of operation. For example, in a voltammetric mode of operation, the AIE of the invention can produce a signal which has a constant peak current or alternatively a constant peak potential relative to the standard hydrogen electrode (SHE) or it may have both fixed peak current and fixed peak potential (relative to the SHE). This signal can then be used as an internal standard from which the signal at the WE produced due to the presence of some target analyte(s) may be calibrated. Because this signal is constant relative to a known fixed quantity, such as the SHE, it may be used in practice with a less stable reference electrode such as a PRE thus providing a stable signal for internal calibration without the use of a conventional reference electrode.

In one aspect, the invention provides a multi-phase AIE for use in a voltammetric and/or amperometric electrochemical sensor system for measuring the presence and/or concentration of an analyte in a sample. The AIE provides a predictable analyte-insensitive signal which is used as a standard of comparison for the signal generated using an ASM at the working electrode, and thereby allows an end user to determine an analyte's presence and/or concentration. An advantage of embodiments of this aspect of the invention is that it provides a self-calibration means, and thereby obviates any need for repeated calibration by the end user.

The AIE provided by the invention can include the following components: an electrolytic layer, a redox active material (RAM), a conductive component, and, optionally, a conductive physical barrier. In some embodiments, one or more of these components may be combined together. For instance, the RAM may be dispersed in the electrolytic layer and/or the electrolytic layer may saturate the pores of the conductive physical barrier. In other embodiments, the AIE optionally includes more than one of any one or more of the components described above.

Conductive Physical Barrier

The conductive physical barrier, when present, serves to separate physically the other components of the AIE from the analyte. This physical separation attenuates the direct chemical interaction of the remainder of the AIE with the analyte, thereby minimizing effects such as convective mixing between the analyte and electrolytic layer. This in turn minimizes the change in composition of the electrolytic layer due to interaction with the analyte. A requirement of the conductive physical barrier is that it effectively conducts the current necessary for generating the electrical signal associated with the redox active material.

Some embodiments of the invention have a single conductive physical barrier between the electrolytic layer and the analyte, while other embodiments include additional conductive physical barriers that serve to separate physically but maintain electrical contact between multiple electrolytic layers within the AIE. In other embodiments of the invention, a conductive physical barrier is present at the open end of the AIE housing, interposed between the sample and the contents of the AIE cavity, to contain the contents within the AIE cavity. In another embodiment, one or more internal conductive physical barriers are present within the AIE cavity, at the interface between any two of the component phases within the AIE cavity, to separate those two phases from each other physically.

Selection criteria for the conductive physical barrier include but are not limited to tensile strength, wettability and porosity. Suitable materials include, but are not limited to, membranes, porous frits, and films. In some embodiments, the conductive physical barrier comprises a RAM. For example, the RAM may be dispersed in a conductive physical barrier. In some embodiments, a conductive physical barrier is a membrane containing an IL containing the RAM. In other embodiments, the conductive barrier is a polyethersulfone membrane. In another embodiment, the conductive physical barrier is a PVDF (polyvinylidene difluoride) membrane. Additional embodiments may combine the conductive physical barrier with the electrolytic layer into one component.

Electrolytic Layer

The electrolytic layer (e.g. composed of an RTIL or other suitable material, as described herein) provides the constant chemical environment and ionic strength for the RAM and provides a layer that limits or eliminates direct chemical interaction of the RAM with the sample being analyzed. Selection criteria for the electrolytic layer include (a) that its component composition must remain substantially unchanged over the lifetime of the AIE, (b) that it effectively conducts the current necessary for generating the electrical signal associated with the redox active material, and, optionally, (c) that it be substantially immiscible with the sample being analyzed.

In some embodiments, the electrolytic layer is comprised of a fluorous layer with a dispersed electrolyte. Suitable fluorous organic liquids include but are not limited to perfluoroaromatic compounds (e.g. hexafluorobenzene), perfluoroalkanes (e.g. tetradecafluorohexane, octadecafluorooctane, eicosafluorononane, and decafluoropentane) and alkyl perfluoroalkyl ethers (e.g. nonafluorobutyl methyl ether). The dispersed electrolyte for the fluorous layer can be but is not limited to a fluorous ionic liquid (for examples see: *Chem. Comm.* 2000, 2051-2052, incorporated herein by reference).

In some embodiments, the electrolytic layer is a fluorous phase comprising a fluorous organic liquid and a dispersed electrolyte that is adjacent to but substantially immiscible with the sample. In various embodiments, the fluorous phase is at least 50% or at least 90% by weight of one or more fluorous organic compounds and the balance of the phase is comprised of one or more diluents including but not limited to gelling agents, electrolytes, organic solvents, water, inorganic compounds including salts, organic compounds, carbon allotropes, and redox active materials. In some embodiments of the invention, more than one fluorous phase may be present.

In some embodiments, the electrolytic layer is comprised of an organic layer with a dispersed electrolyte. For example, a phase transfer agent dissolved in a common organic solvent (e.g. tetrabutyl ammonium bromide in toluene) is a suitable electrolytic layer.

In some embodiments, the electrolytic layer is an organic phase comprising an organic liquid adjacent to but substantially immiscible with the sample. In various embodiments, the composition of the organic phase is at least 50% or at least 90% by weight of one or more organic compounds and the balance of the phase is comprised of one or more diluents including but not limited to gelling agents, electrolytes, water, inorganic compounds including salts, organic compounds, carbon allotropes, and redox active materials. In some embodiments of the invention, more than one organic phase may be present.

In some embodiments, the electrolytic layer is comprised of an aqueous layer with a dispersed electrolyte. The aqueous layer is comprised substantially of water but may also include one or more diluents including but not limited to gelling agents, organic solvents, inorganic compounds including salts, organic compounds, carbon allotropes, and redox active materials. The dispersed electrolyte comprises a salt of anions and cations chosen from a group including but not limited to inorganic, organic, and/or polymeric ions. In one embodiment the dispersed electrolyte is potassium chloride.

Due to the inherent low volatility of ionic liquids (ILs) and their ionic, and therefore, electrically conductive nature, ILs meet the criteria described above for electrolytic layers and so are employed in various embodiments of the invention. In some embodiments of the present invention, the electrolytic layer phase generally includes at least one IL that is substantially immiscible with the sample or with any intermediary electrolytic layers or phases, when such phases are present. This quality of substantial immiscibility may be achieved as a result of the intrinsic properties of the IL itself, or may be the result of components such as a conductive physical barrier present in the construct (e.g. a porous frit) separating the phases or a membrane separating the phases. The particular components of the IL phase may be chosen to achieve desired characteristics, which may include but are not limited to sample immiscibility; temperature stability; viscosity, dielectric constant; specific ionic chemical composition, and phase state at temperatures characteristic of particular applications.

In some embodiments, the IL components are chosen so as to be liquid at a temperature or within a range of temperatures that include the temperature within which the sample will be measured. Suitable temperature ranges include but are not limited to between 10 degrees to 50 degrees Celsius; alternately from about 16 degrees to about 45 degrees Celsius; alternately from about 20 degrees to about 40 degrees Celsius.

In one embodiment, the electrolytic layer is an ionic liquid (IL) composed of an anionic chemical species and a cationic chemical species and located adjacent to the sample but substantially immiscible with the sample. In various embodiments, the composition of the IL phase is at least 50% or at least 90% by weight of one or more ionic liquids and the balance of the phase is comprised of one or more diluents including but not limited to gelling agents, electrolytes, organic solvents, water, inorganic compounds including salts, organic compounds, carbon allotropes, and redox active materials, In some embodiments, the composition of the IL phase is 100% of one or more ionic liquids. Illustrative IL cations include but are not limited to quaternary pyrrolidines and N,N'-disubstituted imidazoles. Illustrative IL anions include but are not limited to imides and borates, phosphates, and sulphates, which may be substituted as appropriate to form an anion of interest.

In various embodiments, the IL cation is selected from a group that includes but is not limited to imidazolium (for example, 1-butyl-3-methylimidazolium, $C_4$mim), pyridinium (for example, N-butyl pyridinium ($C_4$py)), pyrrolidinium (for example, N-butyl-N-methyl pyrrolidinium ($C_4$mpyrr)), tetraalkylammonium, and tetraalkylphosphonium. In various aspects, the IL anion is selected from a group that includes but is not limited to tetrafluoroborate ($BF_4$), bis(trifluoromethanesulfonyl)imide ($N(Tf)_2$), thiocyanate (SCN), dicyanamide ($N(CN)_2$), ethyl sulphate (($EtSO_4$), hexafluorophosphate, ($PF_6$) and trifluorotris(pentafluoroethyl)phosphate (FAP). In one embodiment, the IL is an RTIL. In some embodiments, the RTIL phase is N-butyl-N-methyl pyrrolidinium bis(trifluoromethanesulfonyl)imide ([$C_4$mpyrr][$N(Tf)_2$]).

In some embodiments, the electrolytic layer comprises a microporous material wherein the IL or RTIL is immobilized within its interconnected micropores. For example, silica based sol-gels can be formed in the presence of ILs resulting in an ionogel which is conductive as a result of the IL contained therein (for example see: *Chem. Mater.*, 2006, 18 (17), pp 3931-3936, incorporated herein by reference).

Alternate microporous materials suitable for use in the AIEs of the invention include those well known in the field of synthetic membranes. Membranes used for selective separations cover a broad range of pore sizes ranging from micrometers to nanometers, and may be derived from organic materials, especially polymers. For example, microporous membranes based on polysulfone, polyethersulfone, polyvinylidenefluoride, polytetrafluoroethylene, and certain derivatives based on those polymers generally exhibit good chemical stability toward both typical analyte solutions and the RTIL, and are thus suitable media for immobilizing the RTIL In this case the RTIL is the principal conduit of charge transfer across the electrolytic layer.

Yet another embodiment of the electrolytic layer is a thin layer of nonporous solid material, for example a polymer film, in which the RTIL exhibits some solubility. The polymer film containing dissolved RTIL can be considered as a solid solution, in that it exhibits the ionic conducting characteristic of the RTIL, but retains the dimensional stability of a solid. Compared to a microporous structure, which must have a minimum thickness to retain a liquid effectively, a nonporous solid solution film can be made extremely thin without developing defects or pinholes. Examples of suitable nonporous polymer films include, but are not limited to, cross-linked derivatives of polyimidazole, poly(vinyl alcohol), poly(vinyl acetate), poly(ethylene oxide), and their copolymers or blends. Conductivity in the solid solution film may be established at different loading, or concentration, of RTIL in different polymers. Non-cross-linked polymers may be used where a relatively low loading of RTIL is sufficient to obtain conductivity. Cross-linked polymers are preferred at relatively high loadings of RTIL to prevent excessive swelling or dissolution. In this case the solid solution of RTIL is a substantially uniform conduit of charges. The solid solution film can be surface-modified to manipulate its selectivity toward hydrogen ions.

The AIE optionally includes an additional electrolytic layer. In one embodiment, an electrolytic layer is adjacent to the sample, and an additional electrolytic layer is interposed between any of the other phases of the electrode. Optionally, two electrolytic layers may be adjacent to each other. Selection criteria for the additional electrolytic layer include the criteria described above for electrolytic layers. Selection criteria for an additional electrolytic layer composition include but are not limited to viscosity and dielectric constant. Exemplary materials include but are not limited to materials as described above for the first electrolytic layer, an ionic liquid, an aqueous electrolyte solution, a gelled aqueous electrolyte solution, an electrolyte containing sol-gel, an electrically conductive sol-gel, an organic solvent, and an organic electrolyte solution.

Optionally, an electrolytic layer comprises one or more RAMs. RAMs suitable for use in an electrolytic layer include, but are not limited to, the RAMs described below.

Redox Active Materials (RAMs)

Selection criteria for suitable RAMs that are a component of the AIE of the present invention include, but are not limited to, oxidation and/or reduction peaks obtained during voltammetric and/or amperometric measurements which are well-defined and are either substantially constant or vary in a definable manner. As discussed above, either an AIM or an ASM can be used in the AIE of the invention. In the AIE, an ASM is effectively transformed into an AIM due to being isolated from the sample by the electrolytic layer. For example, AQ and PAQ are ASMs, but if they are isolated from any test solution either by being dispersed in the electrolytic layer or in contact with an aqueous phase of fixed pH behind the electrolytic layer, and the electrolytic layer (e.g the RTIL) prevents the transfer of protons, then there is one fixed signal (the non-aqueous voltammetry of AQ or PAQ in the electrolytic layer) or the usual (but constant) signal in the aqueous layer. Hence the ASM would then be considered an AIM within the context of this embodiment of the invention. The AIE construct thus confers analyte insensitivity to an ASM.

Suitable redox active materials for use in the AIE of the present invention are reversible, quasi-reversible and irreversible redox-active compounds, including but not limited to redox-active organic molecules, redox-active polymers, metal complexes, organometallic species, metals, metal salts or semiconductors, present as liquids or solids formed as bulk materials, microparticles or nanoparticles, that undergo one or more electron transfer processes not involving reaction with the target analyte and whose redox behaviors are therefore insensitive to the presence of the target analyte. As noted above, an ASM can also be used to form the AIE of the invention if it is isolated from the sample by the electrolytic layer.

In various embodiments of the invention, the RAM is selected from compounds that include but are not limited to, ferrocene or ferrocene derivatives including but not limited to ferrocene derivatives comprising alkyl, aryl and heteroatomic substituents on one or both cyclopentadienyl rings; polymers of variable cross-linking comprising ferrocene and other non-redox-active monomers such as styrene and acrylates, silver nanoparticles on carbon substrates such as glassy carbon, graphite, and carbon nanotubes (CNTs), hexacyano iron compounds with variable counter-ions including but not limited to main group and transition metal cations, and other redox-active transition metal complexes.

In various embodiments, the RAM is n-butyl-ferrocene, silver nanoparticle modified glassy carbon powder (AG-np-GC), ferrocene, polyvinylferrocene, nickelhexacyanoferrate, ferrocene styrene copolymers, ferrocene styrene cross-linked copolymers, Ni Cyclam, or $K_4Fe(CN)_6$. In some embodiments, the AIM is n-butyl-ferrocene. In another embodiment, the AIM is $K_4Fe(CN)_6$. This list is not exhaustive and is not intended to be limiting. One skilled in the art will be able to identify and use many other RAMs in place of or in addition to those listed above.

As discussed above, an ASM can serve the same function as an AIM in the AIE construct. Suitable ASMs for use in the AIE include but are not limited to anthraquinone (AQ), anthracene, 9,10-phenanthrenequinone (PAQ), 1,4-benzoquinone, 1,2-benzoquinone, 1,4-napthaquinone, 1,2-napthaquinone, N,N'-diphenyl-p-phenylenediamine (DPPD), azo containing compounds such as azobenzene and derivatives thereof, porphyrins and derivatives thereof such as octaethylporphyrin or tetraphenylporphyrins, metalloporphyrins and derivatives thereof such as hemin, iron octaethylprophyrin, iron tetraphenylporphyrin, and viologens and derivatives thereof such as methyl viologen. This list is not exhaustive and is not intended to be limiting. One skilled in the art will be able to identify and use many other ASMs in place of or in addition to those listed above.

One or more RAMs may be dispersed in one or more of any of the electrolytic layers (e.g the IL) or the external conductive physical barrier or the conductive component, or may be dispersed in an internal conductive physical barrier. In other embodiments, a single RAM is dispersed in one or more of the electrolytic layers (e.g. the IL) or in the conductive component. In another embodiment, different RAMs are dispersed in one or more electrolytic layers or in the conductive component.

Conductive Component

The AIE of the current invention includes a conductive component. In some embodiments, the conductive component is a conductive backing located at the rear of the AIE cavity and forming the rear wall of the cavity. A conductive lead (sometimes referred to herein as a transmission element) is electrically connected to the backing (i.e. by being soldered to the backing), and protrudes through the rear bore, which may optionally be sealed with one or more materials including but not limited to a silicone polymer, including a substituted silicone polymer and an epoxy composition. The lead provides a means of transmitting electrical signals to and from the electrode.

A variety of conductive materials may be used for the conductive backing, including but not limited to carbon allotropes and derivatives thereof, transition metals (e.g platinum, gold, and mercury), conductive metal alloys, conductive polymeric compounds and derivatives thereof, semiconductor materials and derivatives thereof, including silicon and derivatives thereof, and additional suitable materials not specifically mentioned.

Optionally, a RAM is associated with the conductive backing by methods including but not limited to abrasive immobilization, adsorption, electrostatic binding or covalent binding to the backing surface. Suitable RAMs for associating with the conductive backing include but are not limited to those specified in the preceding section.

Optionally, the conductive component may comprise a plug of conductive material in addition to or in place of the conductive backing. In the latter case, the transmission element is electrically connected to the plug. In one aspect, the plug contains a binder and at least one electrically conductive material. Suitable binders include but are not limited to epoxy, mineral oil and polymer binders. Suitable conductive materials include but are not limited to graphite, MWCNTs, SWCNTs, glassy carbon, as well as those discussed above as materials useful for the conductive backing.

In other embodiments the plug is a mixture of epoxy and graphite. In another embodiment, the plug is a mixture of epoxy, graphite and MWCNTs. In another embodiment, the plug is a mixture of epoxy, graphite and SWCNTs. In another embodiment, the plug is a mixture of epoxy, graphite and glassy carbon. In another embodiment, the plug is formed using epoxy and MWCNTs. In another embodiment, the plug is formed using epoxy and SWCNTs. In another embodiment, the plug is formed using epoxy and glassy carbon. Optionally, one or more RAMs are present in the composite plug, in addition to the binder and the conductive material. RAMs suitable for associating with or incorporating into the conductive plug include but are not limited to those specified in the preceding section. In some embodiments, the RAM is mixed with the binder and the conductive material. In another aspect, the RAM is associated with one of the components of the composite material, by methods including but not limited to abrasive immobilization, adsorption, electrostatic binding or covalent binding. In other embodiments, the components are combined via mechanical mixing using a mortar and pestle. In another embodiment the components are mixed in an organic solvent.

Exemplary Configurations of the AIE

Figure 4A:
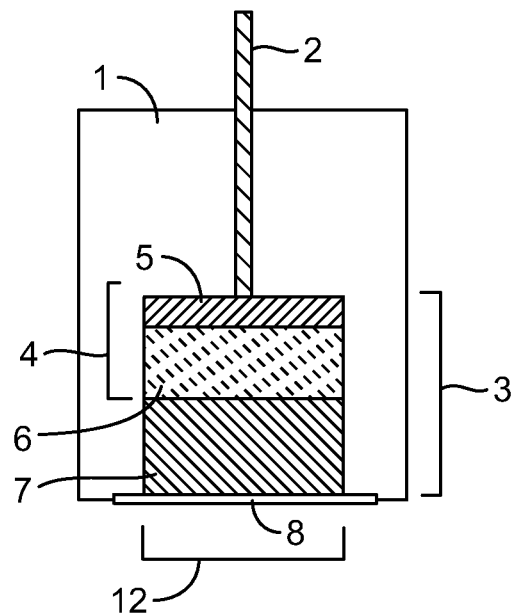
FIGS. 4A and 4B illustrate, in schematic form, exemplary embodiments of the invention. One or more redox active materials may be present in either or both of the composite plug, or the electrolytic layer (e.g. the RTIL phase)
Figure 4B:
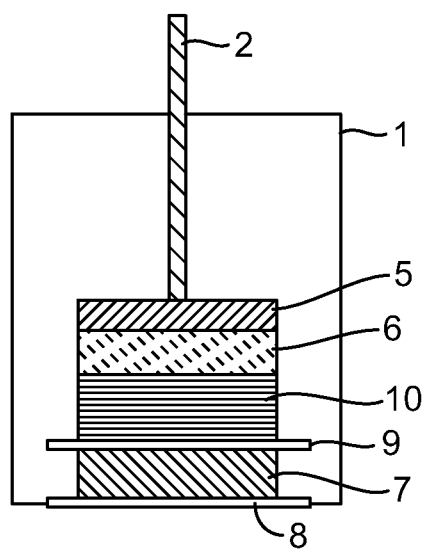

A number of configurations of the component elements of the claimed AIE are possible. Exemplary embodiments are shown schematically in FIGS. 4A and 4B. As shown in FIGS. 4A and 4B with labeled parts, aspects of the AIE include a cylindrical housing (1) with the conductive backing (5) of the conductive component (4) defining an AIE cavity (3) having a sample end (12). A conductive lead (2) is attached and in electrical connection with the conductive plate and protrudes through the rear bore, providing a means for transmitting electrical signals to and from the AIE. The conductive component optionally includes a plug of conductive composite material (6) in the AIE cavity in electrical contact with and adjacent to the conductive backing. A first electrolytic layer (e.g IL phase) (7) is adjacent to the conductive component, and contained within the AIE cavity by a first, external, conductive physical barrier (8). Optionally, additional electrolytic layers (e.g. IL phases) may be present. Optionally, an additional electrolytic layer (10) is located between the conductive component and the first electrolytic layer (e.g. IL phase), and is separated from the first electrolytic layer (e.g. IL phase) by a conductive physical barrier (9). Optionally, additional electrolytic layers may be present.

The RAM may be dispersed in the conductive component, optionally in either the conductive backing and/or the composite plug, or in any of the electrolytic layers (e.g. IL layers).

In operation, the analyte is chemically isolated from the RAM by the electrolytic layer (e.g. IL layer). The RAM may be further chemically isolated or physically isolated from the analyte by an additional electrolytic layer.

Some embodiments of the invention are illustrated in FIG. 4A, as described above. The conductive component (4) includes a conductive composite plug (6) and an electrolytic layer (e.g. an IL phase) (7), contained by an external conductive physical barrier (8). There may be RAM dispersed in the plug or in the electrolytic layer (e.g. IL phase). Optionally, the same or different RAMs are dispersed within both the plug and the electrolytic layer (e.g. IL phase).

In another embodiment of the invention (FIG. 4B), a second electrolytic layer (10) is added between the conductive material plug and the first electrolytic layer (e.g. IL phase). The second electrolytic layer may be in direct contact with the first electrolytic layer (e.g. IL phase); alternatively, a first internal conductive physical barrier (9) may separate the second electrolytic layer from the first electrolytic layer (e.g. IL phase). One or more RAMs may be dispersed in the conductive component or the electrolytic layers (e.g. IL phase).

In one embodiment, the present invention provides a multiphase AIE for use in an electrochemical sensing device for measuring an analyte in a sample, the AIE comprising (a) an electrolytic layer; (b) an electrically conductive component electrically connected to the electrolytic layer, and (c) a redox active material (RAM), capable of being electrically oxidized and/or electrically reduced, wherein the redox activity of the material is substantially insensitive to the analyte, and wherein further the RAM may be dispersed in either the electrolytic layer or the conductive component.

Electrochemical Sensing System

In another aspect, the present invention provides an electrochemical sensor system for measuring the presence and/or concentration of an analyte in a sample. Various embodiments of the invention are possible, which have in common an embodiment of the AIE of the present invention, a working electrode, optionally a counter electrode, a reference or pseudo-reference electrode and a controller device for supplying a range of electrical signals to the indicator and working electrodes, and measuring the electrical response of the working electrode and the AIE over the range of applied signals. These components are discussed in further detail below.

System Component: Analyte Insensitive Electrode

The analyte sensor system of the present invention includes an AIE as described above.

System Component: Working Electrode

The analyte sensing system of the present invention further includes a working electrode. Working electrodes suitable for use in the sensor system of the present invention are known in the art. See U.S. Pat. No. 5,223,117, PCT Patent Publication Nos. 2005/066618 and 2007/034131 and GB Patent Publication No. 2409902. Working electrodes suitable for use in the sensing devices of the invention include, for example and without limitation, those described in provisional U.S. patent application Ser. No. 61/161,139, filed 25 Mar. 9; Ser. No. 61/225,855, filed 15 Jul. 9; and Ser. No. 61/289,318, filed 22 Dec. 9, each of which is incorporated herein by reference.

Characteristic of the working electrode component of the present invention is that it allows the passage of current, in response to electrical perturbations of the sample, and demonstrates an electrochemical response that is sensitive to one or more analyte(s) in the system. Optionally, the WE may be chemically modified with analyte sensitive species or materials. In one aspect, the WE is modified with at least one analyte-sensitive redox active material having well-defined oxidation and/or reduction peaks.

The general mode of operation of working electrodes in an electrochemical sensor system is known in the art. Upon being subjected to an electrical signal (optionally, an applied potential relative to some thermodynamically fixed reference electrode potential), the electrical response of the working electrode is measured and compared to a reference point provided by, for example, an external calibration plot in cases where the WE passes minimal current (potentiometric device), or, in embodiments of the present invention, to a reference point provided by the AIE. In voltammetric mode, the WE response is measured as a function of the potential difference applied between the WE and some suitable CRE/PRE.

System Component: Reference Electrode

The sensor system of the present invention includes a conventional reference electrode or, a pseudo-reference electrode. Examples of conventional reference electrodes and pseudo-reference electrodes are known in the art. See Bard and Faulkner, "Electrochemical Methods: Fundamentals and Applications" (Wiley 2001). In operation, the CRE allows the application of a known, controlled potential difference to the WE by providing a fixed reference point.

In some embodiments, a "pseudo-reference electrode" (PRE) may be used. These typically do not comprise both halves of a well-defined redox potential, and are therefore not thermodynamic reference electrodes of fixed composition and potential. However, they are functionally simpler than a conventional RE and provide a reasonably constant potential over the timescale of an electrochemical experiment. Use of the PRE in conjunction with an AIE of the present invention obviates the need for the conventional reference electrode thereby overcoming the disadvantages of the CRE. One (but not exhaustive) example of a PRE is the use of a silver wire.

System Component: Counter Electrode

Counter electrodes suitable for use in the sensor system of the present invention are known in the art. See, for example, Bard and Faulkner, "Electrochemical Methods: Fundamentals and Applications" (Wiley 2001). Optionally, in order to avoid unwanted electrochemical redox processes occurring at the CE which may interfere with the signal measured at the WE, the CE is typically made of a relatively chemically inert material, commonly Pt or carbon (graphite). In operation, the CE serves as an electron source or sink, thereby delivering current to the sample and allowing it to flow through the sensor system.

System Component: Controller/Processor Device

The analyte sensor system of the present invention further includes a controller/processor device. Controller/processor devices suitable for use in the analyte sensor system of the invention include, for example and without limitation, those described in provisional U.S. patent application Ser. No. 61/161,139, filed 25 Mar. 2009; Ser. No. 61/225,855, filed 15 Jul. 2009; Ser. No. 61/289,318, filed 22 Dec. 2009; Ser. No. 61/308,244, filed 25 Feb. 2010; and Ser. No. 61/309,182, filed 1 Mar. 2010. In other embodiments, the controller/processor device is a single-channel device through which the working electrode and AIE are electrically connected and controlled, and their signals recorded, on the same channel. Examples of single channel controllers include a potentiostat and a galvanostat. In another embodiment of the invention, the working electrode and the AIE are physically remote and connected by a multi-channel device capable of controlling and/or recording signals from the working electrode and the AIE independently. In some embodiments, the controller/processor device is a multichannel potentiostat. In yet another embodiment, the signals from the working electrode and AIE are combined and the processor then analyzes the data from the combined signal. In another embodiment, the signals from the working electrode and AIE are recorded separately and subsequently combined and analyzed by the processor.

Voltammetric Measurement

The electrical responses of the AIE as incorporated in embodiments of the sensor system of the present invention are determined using methods including but not limited to cyclic or square-wave voltammetry as described in the "Materials and Methods" section of the Example below. In operation, upon being subjected to cyclic or square wave voltammetry, embodiments of the present invention give an electrical response that is substantially constant or varies in a substantially predictable manner.

While one important application of the present invention is the measurement of pH, the invention has application in all areas involving voltammetric and amperometric sensing, including but not limited to the detection of metal ions, metal complexes and derivatives (e.g. As(III), Pb(II), Fe(II/III), Cu(II/I), Hg(II), and many others), the detection of pollutants (e.g. chlorinated phenols/organics, pesticides, herbicides, nitrite/nitrate, and the like), gas sensing both directly in air and dissolved gases in aqueous media (e.g. $CO_2$, CO, $SO_2$ and $H_2S$ in particular—important in the petrochemical and automobile industries, among many others), environmental monitoring (WHO, US EPA, and EU regulatory bodies), drug detection (e.g. the OxTox drug testing unit), food industry Q&A (e.g. capsaicin in spicy foods, hesperidin in citrus fruit juices, and the like), medical and (bio)pharmaceutical Q&A, diagnostics/accreditation, and glucose sensing (diabetes, home monitoring). Accordingly, those of skill in the art will recognize that the devices and methods of the present invention are illustrated by but are not limited by the examples that follow.

EXAMPLES

Materials and Methods

Conductive Components

Graphite/Epoxy Composite

A graphite/epoxy composite was prepared by combining 300 mg graphite with 1.15 grams of epoxy A and 150 mg of epoxy B (Epoxy Technology, Bellerica, Md.) using a mortar and pestle.

Multi-Walled Carbon Nanotube (MWCNT)/Graphite/Epoxy Composite with n-butyl-ferrocene A MWCNT/graphite/epoxy composite containing n-butyl-ferrocene was prepared by combining, in dichloromethane, 17 mg of multi-walled bamboo-type MWCNTs (bamboo type 5 to 20 μm in length and having an outer wall diameter of 30+/−15 nm) (Nanolab, Brighton, Mass.) with 17 mg of graphite, 20 mg of n-butyl-ferrocene, 200 mg of epoxy A and 30 mg of epoxy B. The solvent was then evaporated at room temperature.

Room Temperature Ionic Liquid RTIL Phase [$C_4$mpyrr][N(Tf)$_2$]

As described below, [$C_4$mpyrr][N(Tf)$_2$] was used as the RTIL phase in several of the exemplary embodiments.

1% n-butyl-ferrocene in N-butyl, N-methyl-Pyrrolidinium bis(trifluoromethylsulfonyl)imide ([C4mpyrr][N(Tf)$_2$])

A solution of 1% volume:volume n-butyl-ferrocene was prepared by mixing 10 uL of n-butyl-ferrocene in 1.0 mL of [$C_4$mpyrr][N(Tf)$_2$].

Materials and Methods: Electrolytic Layers
2% High Molecular Weight (HMW) Hydroxyethylcellulose Gel with 1M KCl 100 mg of high molecular weight hydroxyethylcellulose was dissolved in 5 mL 1M KCl by stifling the solution over heat (approximately 80° C.) until the hydroxyethylcellulose was completely dissolved.

$K_4Fe(CN)_6$ in 1M KCL 0.755 g of KCl was added to 0.042 g of $K_4Fe(CN)_6$ in 10 mL de-ionized water and mixed by stifling.

Materials and Methods: Analyte Insensitive Electrode (AIE) Construction

A hollow cylindrical housing 3 inches in length and having an inner diameter of 0.140 inches through and a counter-bore of 0.188 inches in diameter and 0.275 inches in depth, was machined from a cast PEEK polymer rod. An internal lip was thereby formed at the point of diameter change. A 20 gauge copper lead soldered to a circular brass disc having the same diameter as the housing's larger internal diameter was then placed within the housing, seated on top of the internal lip. An AIE cavity and a smaller-diameter rear housing cavity were thereby formed, with the brass disc forming the rear wall of the AIE cavity, and the lead extending through the rear bore and protruding externally.

The internal components of the AIE were then assembled. A conductive plug, optionally with a RAM dispersed in it, was first formed within the AIE cavity, on top of the brass plate opposite the brass lead, and flush with the sample end of the housing, by packing the AIE cavity with one of the uncured conductive composite materials described above. After curing (by baking at 150 degrees C. for 1 hour), the exposed end of the plug was cleaned and polished. A polymeric collar having an internal diameter identical to the external diameter of the housing was then fitted over the sample end of the housing, thereby elongating the AIE cavity in which the AIE phase layers were placed.

A first PEEK washer having an internal diameter of 3/16 inch and an outer diameter identical to the internal diameter of the AIE cavity was then placed in the AIE cavity and tamped until flush with the plug, forming a well. A drop of RTIL phase was then deposited in the well, followed by a polyethersulfone membrane (i.e. the conductive physical barrier) having the same diameter as the washer, and a second PEEK washer placed on top of the membrane.

Optionally, the plug is recessed, and the PEEK washer adjacent to the plug is omitted. The RTIL phase is layered directly on the plug surface. A polyethersulfone membrane is then placed over the end of the AIE cavity.

Optionally, an additional electrolytic layer which may optionally comprise an RAM dispersed in it is interposed between the RTIL (i.e. the first electrolytic layer) phase and the sample, by placing one drop of the second electrolytic layer solution in the well formed by the washer adjacent to the composite plug, followed by a polyethersulfone membrane and another PEEK washer.

In other embodiments, a second RTIL phase layer (i.e a second electrolytic layer) which may optionally comprise a RAM dispersed in it is interposed between the first electrolytic layer and the composite plug by placing one drop of the second RTIL phase in the well formed by the washer adjacent to the composite plug, followed by a polyethersulfone membrane and a PEEK washer.

After assembly, the layers were compressed by placing the probe lengthwise in a C-clamp and exerting sufficient pressure to bring the end of the electrode collar and the contents of the housing flush with the edge of the housing's sample.

Test Protocol

Square wave or cyclic voltammetric measurements were made using a standard three-electrode configuration using an ECHOCHEMIE AUTOLAB potentiostat/galvanometer (model PGSTAT12) with the AIE acting as the working electrode, a saturated calomel electrode functioning as a reference, and a graphite rod serving as a counter-electrode. The sample end of the AIE, the sensor end of the calomel reference, and the counter-electrode were placed in contact with a buffer solution of defined pH. The system was then subject to oxidative or reductive cycles of square-wave voltammetry over a range of potentials and the resulting current through the AIE was measured as a function of the applied potential.

EXEMPLARY EMBODIMENTS

First Exemplary AIE Embodiment

A first exemplary AIE having a second electrolytic layer with the RAM in the RTIL phase (i.e. the first electrolytic phase) was constructed as described in the materials and methods section above using a graphite/epoxy plug, 1 drop of 1M KCl for the second electrolytic phase and 1 drop of a 1% volume:volume solution of n-butyl-ferrocene in $[C_4mpyrr][N(Tf)_2]$ for the RTIL phase.

Second Exemplary AIE Embodiment

A second exemplary AIE having an aqueous electrolytic phase and with the RAM in the RTIL phase was constructed in the same manner as the first, with the exception that one drop of 1M KCl in 2% HMW hydroxyethylcellulose gel was used for the second electrolytic phase.

Third Exemplary AIE Embodiment

Figure 2:
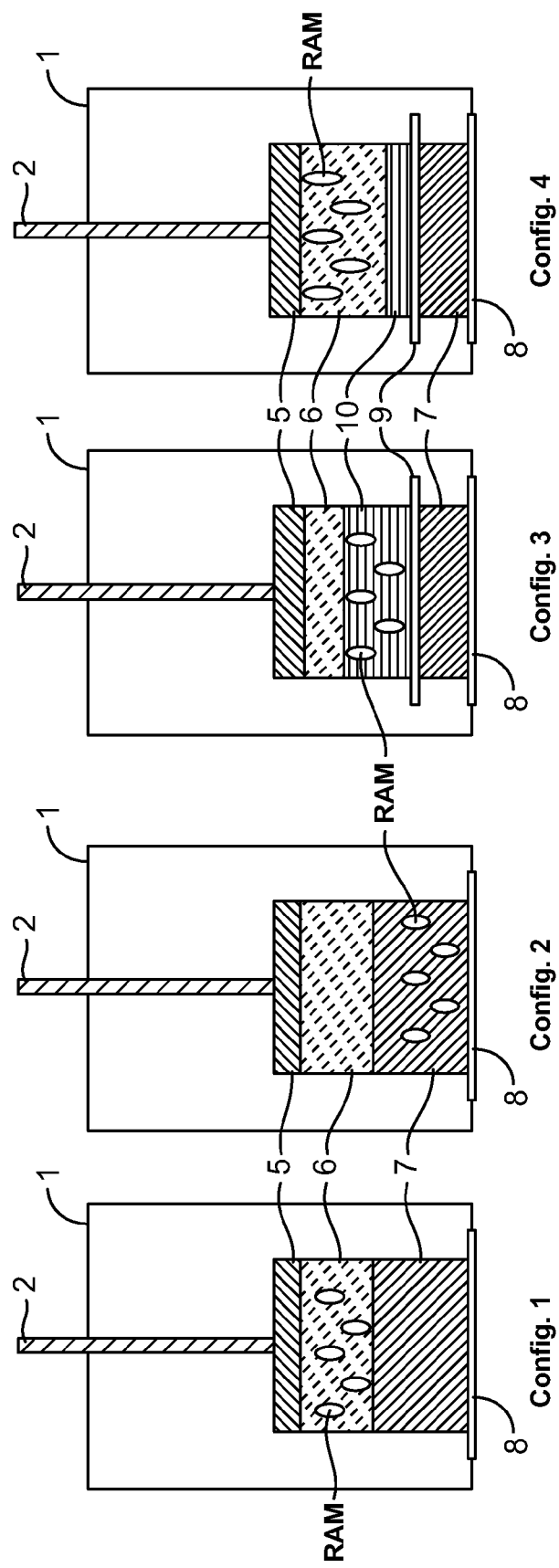
FIG. 2 shows AIE configurations with which various analyte-insensitive materials were tested, as shown in FIG. 3.

A third exemplary embodiment having an aqueous electrolytic phase and with the RAM in the RTIL phase was constructed generally as described in the Materials and Methods section above, using a MWCNT/graphite/epoxy/n-butyl-ferrocene plug prepared with 17 mg MWCNT, 17 mg graphite, 200 mg epoxy A, 30 mg epoxy B and 20 mg of n-butyl-ferrocene. The reagents were combined by stifling in methylene chloride and then evaporating the solvent at room temperature. 1 drop of aqueous 1M KCl was used for the second electrolytic layer, and 1 drop of 1% volume:volume n-butyl-ferrocene in $[C_4mpyrr][N(Tf)_2]$ for the RTIL phase (i.e. the first electrolytic layer). This example is depicted as Configuration 4 in FIG. 2 wherein the RAM is in both the carbon plug and the RTIL.

Figure 5A:
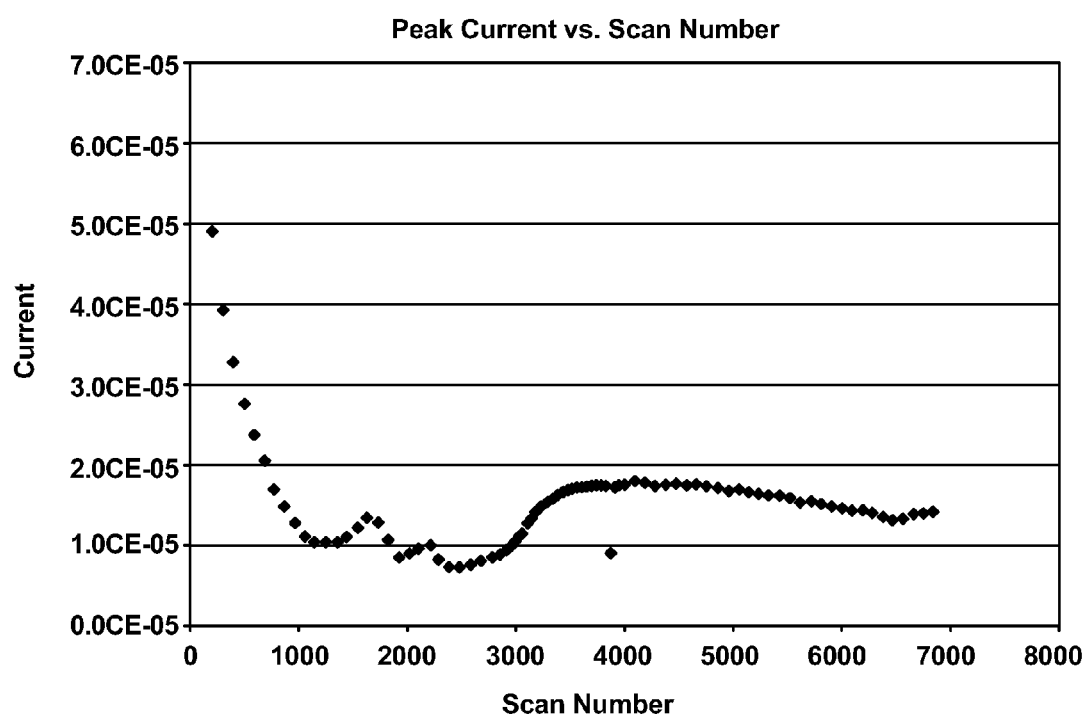
FIGS. 5A, 5B and 5C show results from voltammetric measurements taken from the third exemplary embodiment of the invention.
Figure 5B:
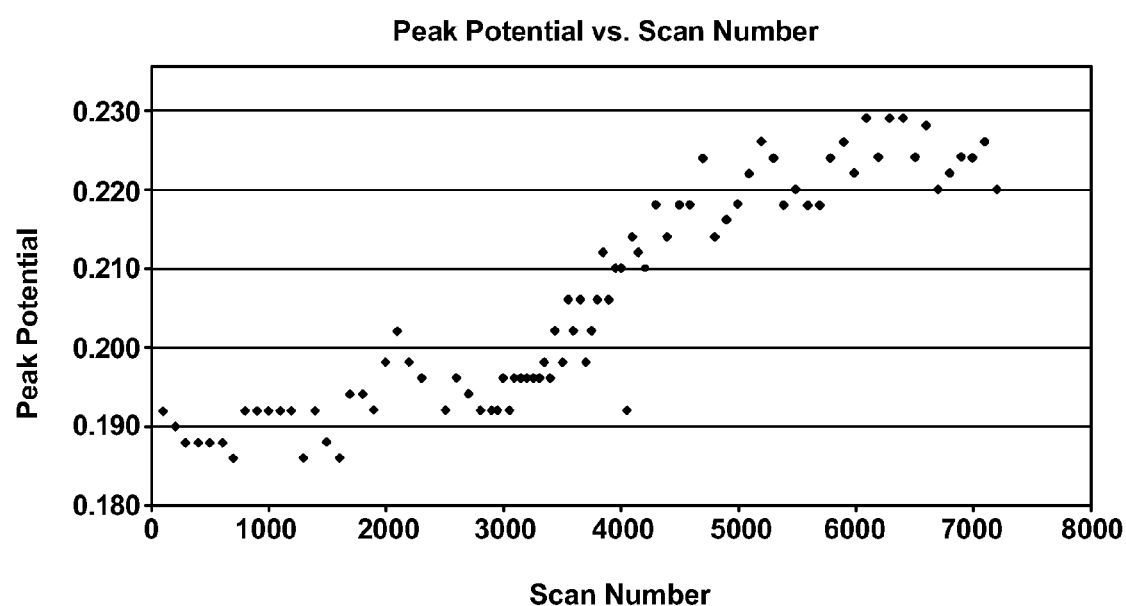

Square wave voltammetric measurements were then made from the third exemplary embodiment as described in the test protocol section above, for a total of 7,000 continuous oxidative cycles of square wave voltammetry over a potential range from negative 0.8 to positive 0.8 volts, and the resulting current through the AIE as a function of the applied potential was measured. The results are shown in FIGS. 5A and 5B. In this experiment, 1000 scans=430 minutes.

Figure 5C:
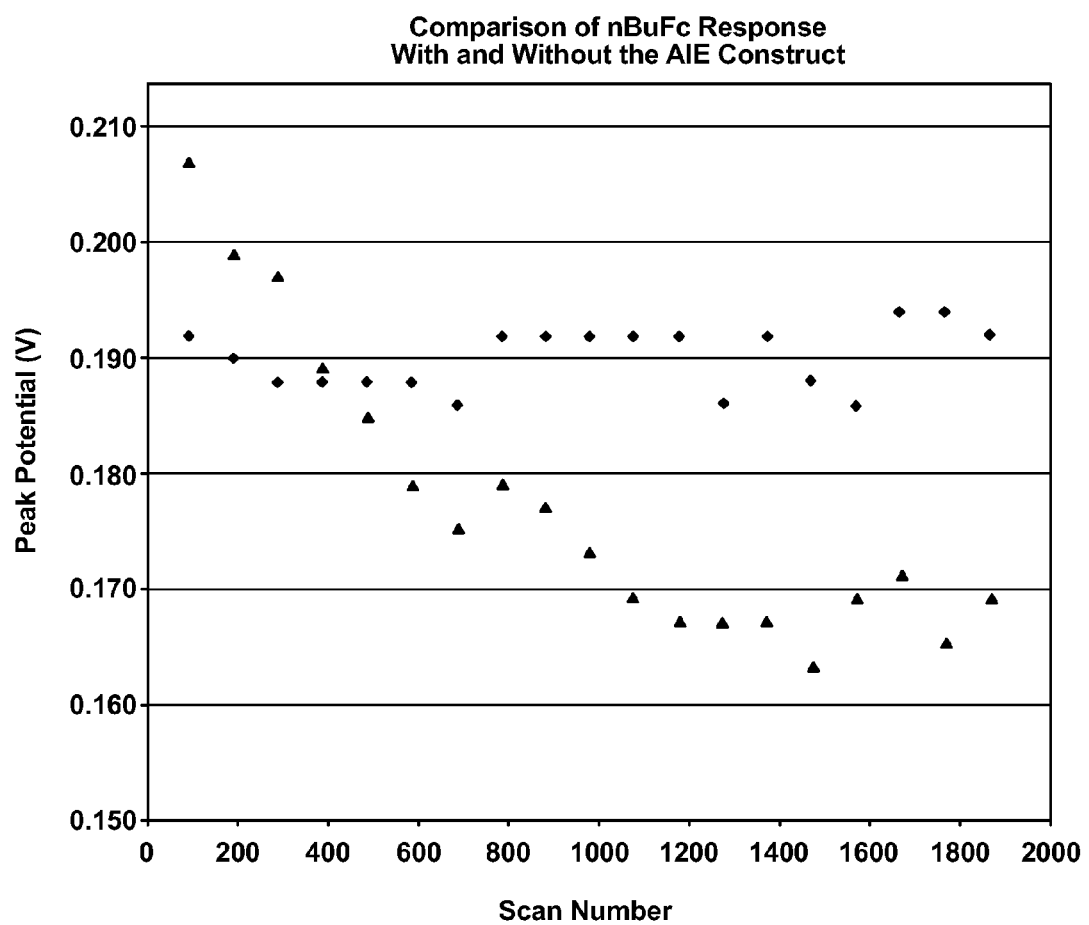

A control experiment was also performed using the construct and materials and square wave measurements described for the third exemplary embodiment with the exception that the electrolytic layers were absent in the construct. FIG. 5C is a plot showing the results from this control experiment in a plot overlayed with the data from the first 2000 scans of the experiment described in the preceding paragraph.

One can see from the data shown in FIG. 5C that the signal derived from the electrode without electrolytic layers in the construct drifts 28 mV in the first 258 minutes (600 scans) (see FIG. 5C) while the corresponding signal derived from the electrode employing the electrolytic layers remained much more stable (drifting less than 5 mV) over the same period of time (see FIG. 5C).

Fourth Exemplary AIE Embodiment

A fourth exemplary AIE having an aqueous electrolytic layer with one RAM in the aqueous electrolytic layer and another, different RAM in the RTIL phase was constructed using the same housing and graphite/epoxy plug as were used in the first embodiment. 1 drop of a solution of 1M KCl and 10 mM $K_4Fe(CN)_6$ was used for the second electrolytic layer, and 1 drop of 1% volume:volume n-butyl-ferrocene in $[C_4mpyrr][N(Tf)_2]$ was used for the RTIL phase.

Fifth Exemplary AIE Embodiment

A fifth exemplary embodiment without a second electrolytic phase but containing a RAM in the composite plug was constructed generally as described in the materials and methods section above using a MWCNT/graphite/epoxy/n-butyl-ferrocene plug prepared by combining 30 mg of n-butyl-ferrocene, 49 mg MWCNT, 49 mg graphite, 575 mg epoxy A and 56 mg epoxy B in methylene chloride, stifling, then evaporating the solvent at room temperature. The plug was recessed slightly in the housing. No washer was used adjacent to the plug; instead, 1 drop of $[C_4mpyrr][N(Tf)_2]$ deposited directly on the recessed plug was used as the RTIL electrolytic layer phase. A polyethersulfone membrane was then used as the conductive physical barrier and layered directly over the RTIL phase, followed by a PEEK washer. This is depicted as configuration 1 in FIG. 2.

Figure 6A:
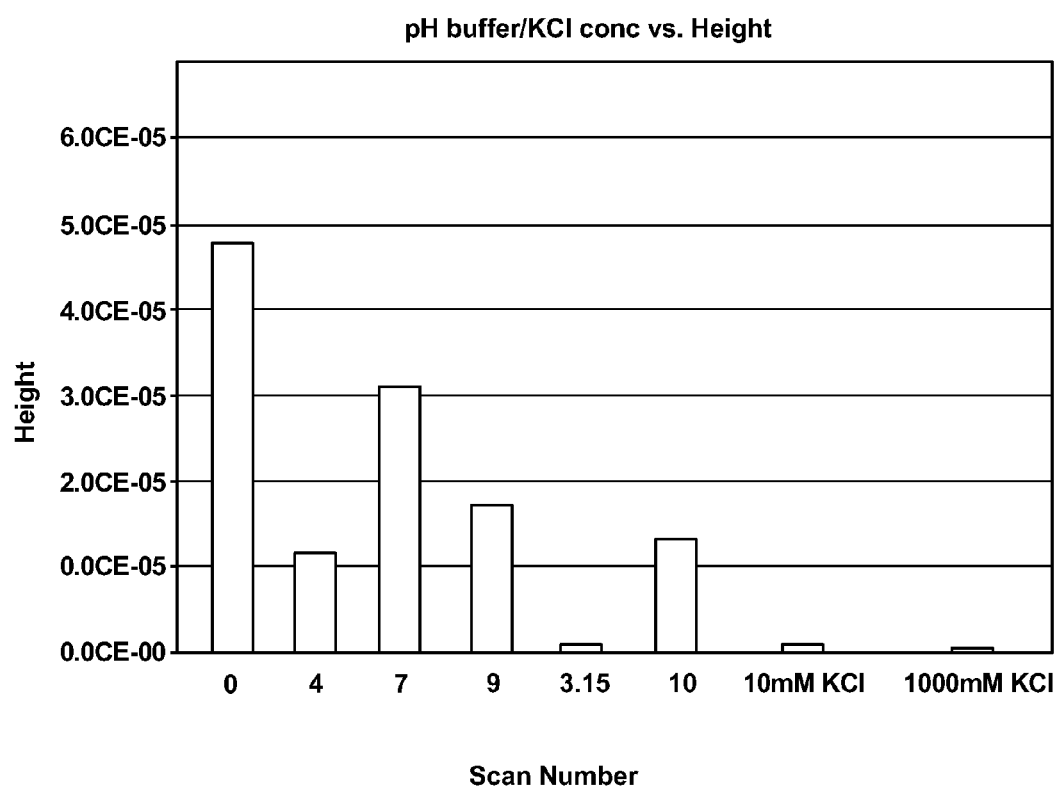
FIGS. 6A, 6B, 6C and 6D show results of voltammetric measurements taken from the fifth exemplary embodiment of the present invention.
Figure 6B:
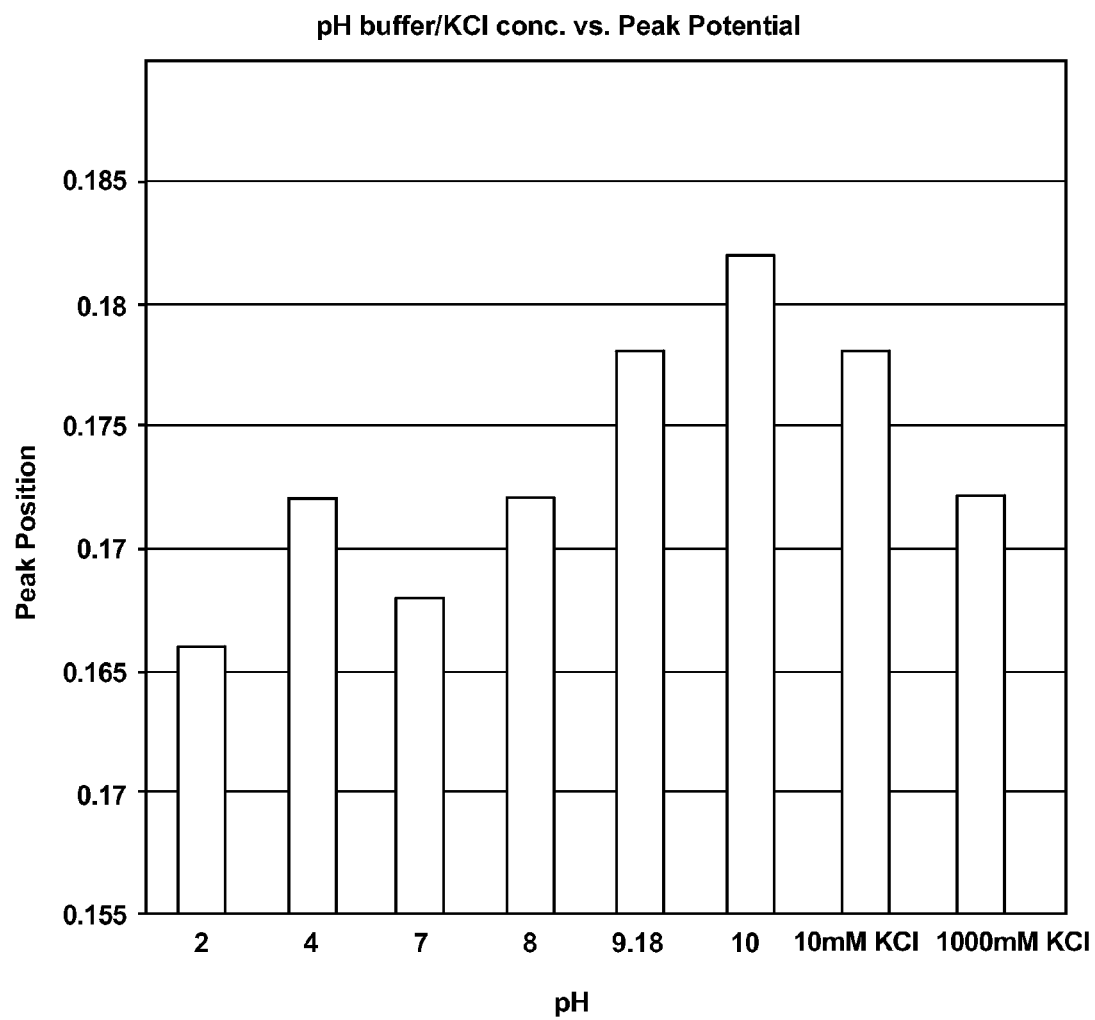

Square wave voltammetric measurements were then made from the fifth exemplary embodiment as described in the test protocol section above, for a total of 20 continuous oxidative cycles of square wave voltammetry over a potential range of −0.8 to +0.8V and the resulting current through the AIE as a function of the applied potential was measured. The measurements were made at pH 2, 4, 7, 8, 9.18 and 10 using buffers having compositions shown in Table 1 and solutions of 10 mM HCl and 1000 mM KCl. The results are shown in FIGS. 6A and 6B.

Figure 6C:
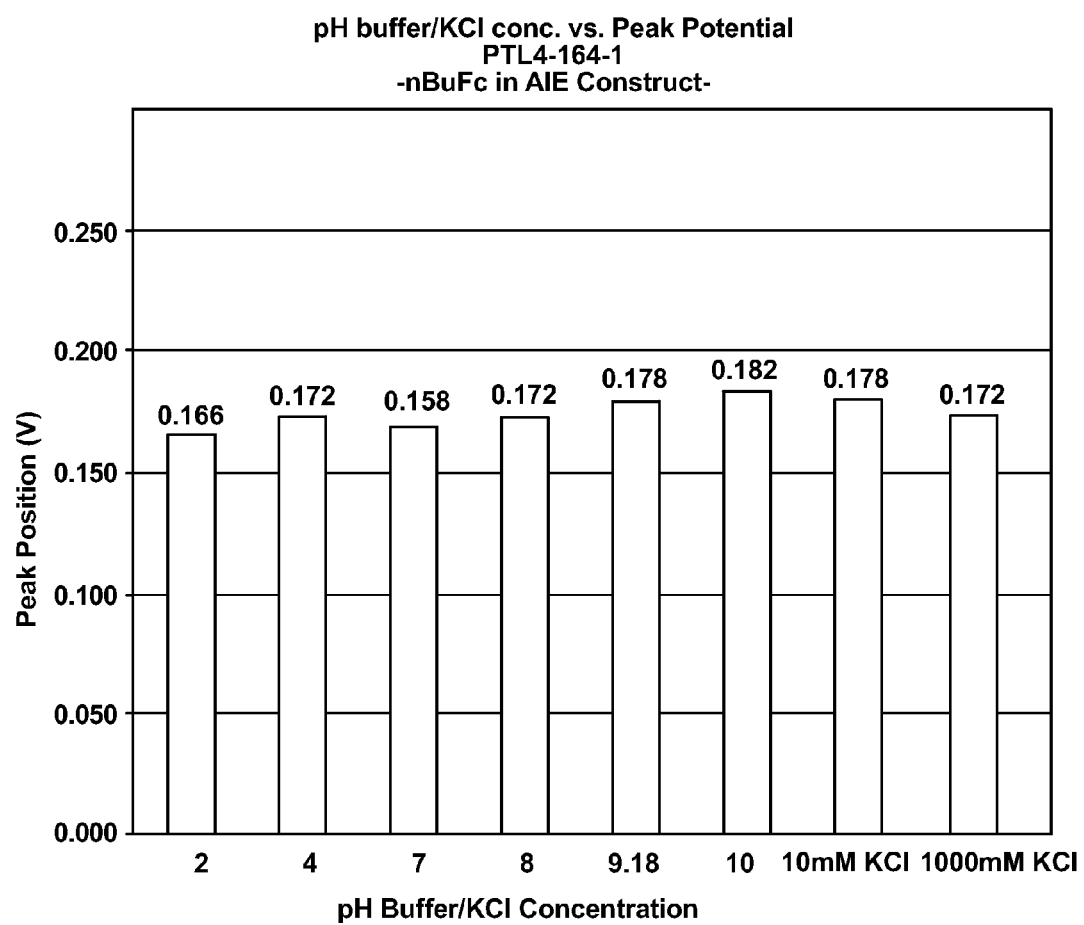

A control experiment was also performed using the construct and materials and square wave measurements described for the fifth exemplary embodiment with the exception that the RTIL electrolytic layer phase and polyethersulfone membrane were absent in the construct. FIG. 6C shows the results from this control experiment.

Figure 6D:
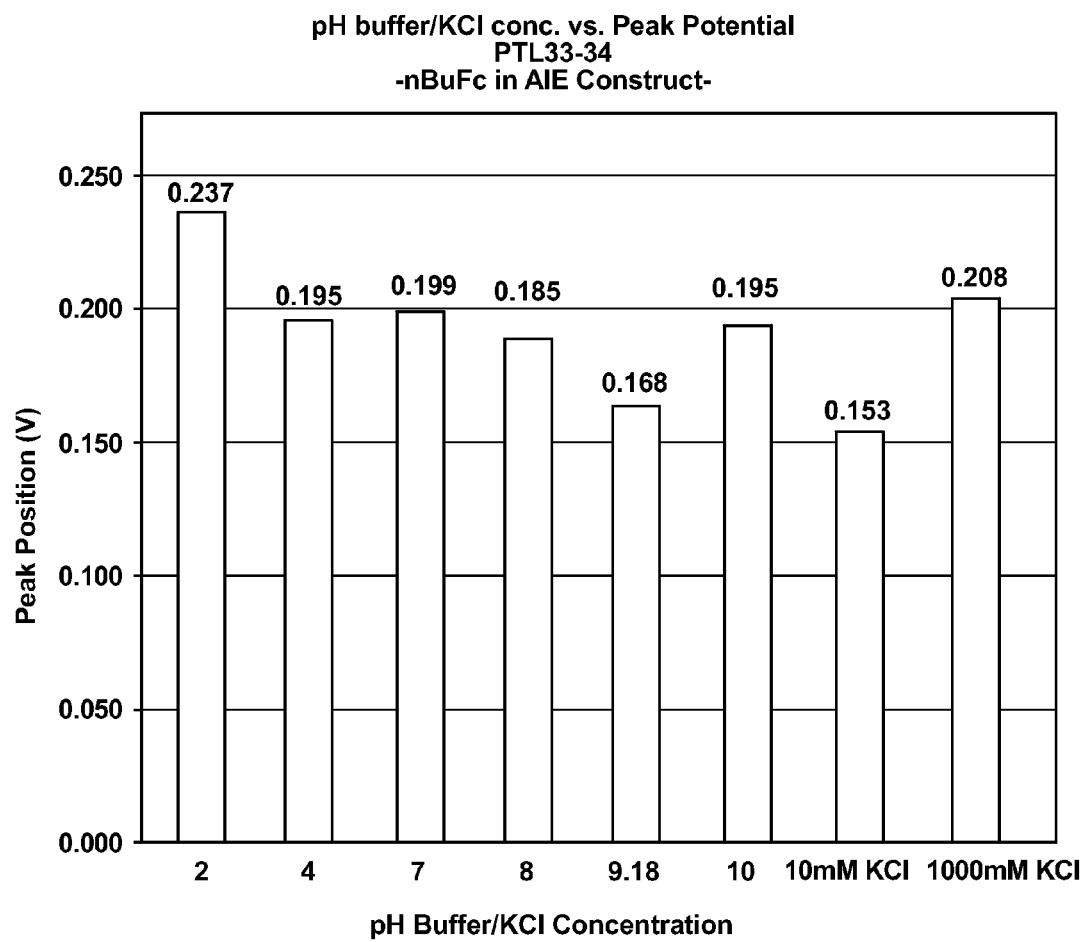

One can see by comparing the results in FIG. 6C and FIG. 6D that the presence of the electrolytic layer (in this case the RTIL) is effective in increasing the stability of the AIE signal across a range of solutions with various compositions. Without the electrolytic layer the signal varied across the samples by 84 mV. While using the AIE construct, the signal varied only 16 mV.

TABLE 1

| Test Buffer Compositions | | | | | |
|---|---|---|---|---|---|
| pH 2 | pH 4 | pH 7 | pH 8 | pH 9.18 | pH 10 |
| glycine HCl | potassium acid phthalate | dibasic sodium phosphate monobasic potassium phosphate | dibasic sodium phosphate monobasic potassium phosphate | sodium borate decahydrate | sodium bicarbonate sodium carbonate |

Sixth Exemplary AIE Embodiment

Figure 7:
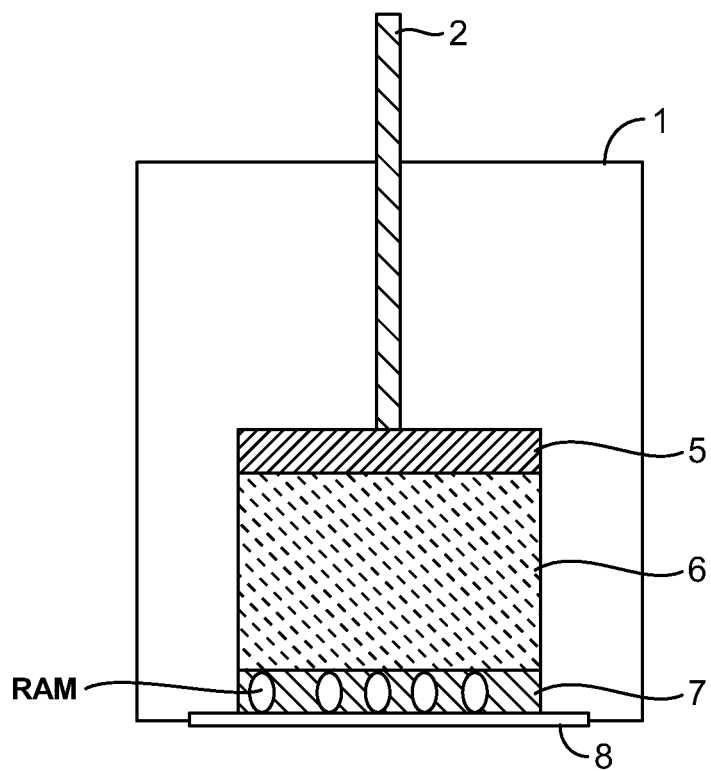
FIG. 7 illustrates, in schematic form, exemplary embodiment 6 of the invention without an intermediary layer and having a RAM in the plug.

A sixth exemplary embodiment without a second electrolytic layer and having the RAM in the plug was constructed with a MWCNT/graphite/epoxy/plug. The PEEK washer adjacent to the plug was omitted; instead, a polyethersulfone membrane wetted with 1% volume:volume solution of n-butyl-ferrocene in $[C_4mpyrr][N(Tf)_2]$ was placed on top of the plug, followed by a PEEK washer, and the electrode was then compressed as described above. This embodiment is depicted in FIG. 7.

These and other embodiments of the invention are provided for illustration and not limitation of the various aspects and embodiments of the invention set forth in the following claims.

What is claimed is:

1. A multi-phase analyte insensitive electrode (AIE) for use in an electrochemical sensing device for measuring an analyte in a sample, the AIE comprising
   (a) an electrolytic layer;
   (b) an electrically conductive component electrically connected to the electrolytic layer;
   (c) a redox active material capable of being at least one of electrically oxidized and electrically reduced, the redox active material being dispersed in at least one of the electrolytic layer and the conductive component, the redox active material being selected from the group consisting of n-butyl-ferrocene, silver nanoparticle-coated glassy carbon, ferrocene, polyvinylferrocene, NiHCF, ferrocene styrene copolymers, ferrocene styrene cross-linked copolymers, Ni Cyclam, and $K_4Fe(CN)_6$, anthraquinone (AQ), anthracene, 9,10-phenanthrenequinone (PAQ), 1,4-benzoquinone, 1,2-benzoquinone, 1,4-napthaquinone, 1,2-napthaquinone, N,N'-diphenyl-p-phenylenediamine (DPPD), azo containing compounds, azobenzene and derivatives thereof, porphyrins and derivatives thereof, octaethylporphyrin, tetraphenylporphyrins, metalloporphyrins and derivatives thereof, hemin, iron octaethylprophyrin, iron tetraphenylporphyrin, and viologens and derivatives thereof, methyl viologen, a redox-active organic molecule, redox-active polymers, metal complexes, organometallic species, metals, metal salts, or semiconductors, and wherein the redox active material undergoes one or more electron transfer processes; and
   (d) a conductive physical barrier positioned so that it is interposed between the electrolytic layer and a sample when the electrode is in contact with the sample, and that physically separates the electrolytic layer from the sample.

2. The AIE of claim 1, wherein the electrolytic layer is selected from the group consisting of: (i) an ionic liquid (IL) comprising an anionic chemical species and a cationic chemical species; (ii) a fluorous phase comprising a fluorous organic liquid and a dispersed electrolyte; (iii) an organic phase comprising an organic liquid and a dispersed electrolyte; and (iv) an aqueous phase comprising water and a dispersed electrolyte.

3. The AIE of claim 2, wherein the electrolytic layer is at least one of an ionic liquid (IL) and a room temperature ionic liquid (RTIL).

4. The AIE of claim 1, wherein the conductive component comprises an electrically conductive material selected from the group consisting of carbon allotropes and derivatives thereof, transition metals and derivatives thereof, post-transition metals and derivatives thereof, conductive metal alloys and derivatives thereof, silicon and derivatives thereof, conductive polymeric compounds and derivatives thereof, and semiconductor materials and derivatives thereof.

5. The AIE of claim 1, wherein the conductive component further comprises a composite material comprising a binder and an electrically conductive material.

6. The AIE of claim 5, wherein the electrically conductive material comprises at least one of graphite, glassy carbon, multi-walled carbon nanotubes (MWCNTs), single-walled nanotubes (SWNTs), boron-doped diamond, and any combination thereof.

7. The AIE of claim 6, wherein the composite material further comprises the redox active material.

8. The AIE of claim 1, wherein the conductive physical barrier is selectively impermeable to an analyte or to non-analyte species in the sample or both.

9. The AIE of claim 1, wherein the conductive physical barrier is selected from the group consisting of a porous frit, a film, a microporous membrane, and a nonporous membrane comprising a solid solution of IL in a polymeric or inorganic material.

10. The AIE of claim 1, wherein the electrolytic layer is the room temperature ionic liquid (RTIL) N-butyl-N-methyl pyrrolidinium bis(trifluoromethanesulfonyl)imide ($[C_4mpyrr][N(Tf)_2]$); the electrically conductive component is composed of multi-walled carbon nanotubes, graphite, and epoxy; the redox active material (RAM) is n-butyl ferrocene; and the conductive barrier layer is a polyethersulfone membrane in direct contact with and thus saturated by the RTIL.

11. The AIE of claim 1, further comprising a second electrolytic layer.

12. The AIE of claim 1, further comprising:
   (e) a second electrolytic phase adjacent to the first electrolytic layer and substantially immiscible with the first electrolytic layer, wherein the second electrolytic phase is interposed between the conductive component and the first electrolytic layer and is in electrical connection with the first electrolytic layer and the conductive component.

13. The AIE of claim 11, further comprising:
   (f) a second electrolytic phase with a conductive physical barrier interposed between the second and the first electrolytic layers, wherein the redox active material is optionally dispersed in the second electrolytic layer and wherein the second electrolytic phase is interposed between the conductive component and the first electrolytic layer and is in electrical connection with the first electrolytic layer and the conductive component.

14. The AIE of claim 12, further comprising a second electrolytic layer.

15. The AIE of claim 14, wherein the second electrolytic layer is selected from the group consisting of an aqueous electrolyte solution, a gelled aqueous electrolyte solution, a electrolytic sol gel, an ionic liquid, a electrolyte containing fluorous layer, and an organic electrolyte solution.

* * * * *